US006984495B2

(12) United States Patent
Thompson

(10) Patent No.: US 6,984,495 B2
(45) Date of Patent: Jan. 10, 2006

(54) HUMAN HAIRLESS GENE AND PROTEIN

(75) Inventor: Catherine C. Thompson, Baltimore, MD (US)

(73) Assignee: Carnegie Institution of Washington, Washington, DC (US)

( * ) Notice: Subject to any disclaimer, the term of this patent is extended or adjusted under 35 U.S.C. 154(b) by 425 days.

(21) Appl. No.: 10/024,368

(22) Filed: Dec. 21, 2001

(65) Prior Publication Data

US 2003/0027300 A1 Feb. 6, 2003

Related U.S. Application Data

(62) Division of application No. 09/287,354, filed on Apr. 7, 1999, now Pat. No. 6,348,348.
(60) Provisional application No. 60/080,888, filed on Apr. 7, 1998.

(51) Int. Cl.
*G01N 33/53* (2006.01)
*C07K 14/00* (2006.01)

(52) U.S. Cl. ............................ 435/7.1; 530/350; 514/2
(58) Field of Classification Search ................. 530/350; 514/2; 435/7.1
See application file for complete search history.

(56) References Cited

U.S. PATENT DOCUMENTS 6,348,348 B1 * 2/2002 Thompson ............... 435/320.1

OTHER PUBLICATIONS

Ahmad et al. (Jan. 30, 1998; Science 279:720–724).*
By Cachon–Gonzalez et al. ( (1994; PNAS 91:7717–7721).*
Thompson (Dec. 15, 1996; J. Neurosci. 16(24):7832–7840).*

* cited by examiner

*Primary Examiner*—Karen Cochrane Carlson
(74) *Attorney, Agent, or Firm*—Morgan, Lewis & Bockius LLP

(57) ABSTRACT

The novel nucleotide sequence and deduced amino acid sequence of the human Hairless gene and protein, respectively, are disclosed. A Hairless expression construct may be used in transcription assays. Moreover, processes of making and using the aforementioned products in screening assays which affect Hairless-regulated transcription are disclosed. Kits comprising a polynucleotide, polypeptide, specific binding molecule, or combinations thereof are disclosed.

17 Claims, 13 Drawing Sheets

FIG. 1A

```
        1                                                   50
        |                                                    |
Human   .......... .......... .......... .......... ..........
Ahmad   .......... .......... ......MEST PSFLKGTPTW EKTAPENGIV
Chichon .......... .......... ......MEST PSFLKGTPTW EKTAPENGIV
Rat     MGLRSSCFVL TLQDPPLGEP HEGRRVMESM PSFLKDTPAW EKTAPVNGIV
Mouse   .......... .......... ......MESM PSFLKDTPAW EKTAPVNGIV

        51                                                 100
        |                                                    |
Human   .......... .......... .......... .......... ..........
Ahmad   RQEPGSPPRD GLHHGPLCLG EPAPFWRGVL STPDSWLPPG FPQGPKDMLP
Cichon  RQEPGSPPRD GLHHGPLCLG EPAPFWRGVL STPDSWLPPG FPQGPKDMLP
Rat     GQEPGTSPQD GLHHGALCLG EPVPFWRGVL SAPDSWLPPG FLQGPKDTLS
Mouse   GQEPGTSPQD GLRHGALCLG EPAPFWRGVL STPDSWLPPG FLQGPKDTLS
```

FIG. 1B

```
           101                                                   150
           |                                                       |
Human      .......... .......... .......... .......... ..........
Ahmad      LVEGEGPQNG ERKVNWLGSK EGLRWKEAML THPLAFCGPA CPPRCGPLMP
Cichon     LVEGEGPQNG ERKVNWLGSK EGLRWKEAML THPLAFCGPA CPPRCGPLMP
Rat        VVEGEGSRNG ERKANWLGSK EGLRWKEAML AHPLAFCGPA CPPRYGPLIP
Mouse      LVEGEGPRNG ERKGSWLGGK EGLRWKEAML AHPLAFCGPA CPPRYGPLIP

           151                                                   200
           |                                                       |
Human      .......... .......... .......... .......... ..........
Ahmad      EHSGGHLKSD PVAFRPWHCP FLLETKILER APFWVPTCLP PYLVSGLPPE
Cichon     EHSGGHLKSD PVAFRPWHCP FLLETKILER APFWVPTCLP PYLVSGLPPE
Rat        EHSSGHPKSD PVAFRPLHCP FLLETKILER APFWVPTCLP PYLMSSLPPE
Mouse      EHSGGHPKSD PVAFRPLHCP FLLETKILER APFWVPTCLP PYLMSSLPPE
```

FIG. 1C

```
          201                                                 250
          |                                                     |
Human     .......... .......... .......... .FYYKDPSIP RLAKEPLAAA
Ahmad     HPCDWPLTPH PWVYSGGQPK VPSAFSLGSK GFYYKDPSIP RLAKEPLAAA
Cichon    HPCDWPLTPH PWVYSGGQPK VPSAFSLGSK GFYYKDPSIP RLAKEPLAAA
Rat       RSYDWPLAPS PWVYSGSQPK VPSAFSLGSK GFYHKDPNIL RPAKEPLAAS
Mouse     RPYDWPLAPN PWVYSGSQPK VPSAFGLGSK GFYHKDPNIL RPAKEPLA..

          251                                                 300
          |                                                     |
Human     EPGLFGLNSG GHLQRAGEAE RPSLHQRDGE MGAGRQQNPC PLFLGQPDTV
Ahmad     EPGLFGLNSG GHLQRAGEAE RPSLHQRDGE MGAGRQQNPC PLFLGQPDTV
Cichon    EPGLFGLNSG GHLQRAGEAE RPSLHQRDGE MGAGRQQNPC PLFLGQPDTV
Rat       ESGMLGLAPG GHLQQACDAE GPSLHQRDGE TGAGRQQNLC PVFLGYPDTV
Mouse     ESGMLGLAPG GHLQQACESE GPSLHQRDGE TGAGRQQNLC PVFLGYPDTV
```

FIG. 1D

```
           301                                                   350
           |                                                       |
Human      PWTSWPACPP GLVHTLGNVW AGPGDGNLGY QLGPPATPRC PSPEPPVTQR
Ahmad      PWTSWPACPP GLVHTLGNVW AGPGDGNLGY QLGPPATPRC PSPEPPVTQR
Cichon     PWTSWPACPP GLVHTLGNVW AGPGDGNLGY QLGPPATPRC PSPEPPVTQR
Rat        PRTPWPSCPP GLVHTLGNVW AGPGSNSFGY QLGPPVTPRC PSPGPPTPPG
Mouse      PRAPWPSCPP GLVHSLGNIW AGPGSNSLGY QLGPPATPRC PSPGPPTPPG

           351                                                   400
           |           *                                           |
Human      GCCSSYPPTK GGDLGPCGKC QEGLEGGASG ASEPSEEVNK ASGPRACPPS
Ahmad      GCCSSYPPTK GGDLGPCGKC QEGLEGGASG ASEPSEEVNK ASGPRACPPS
Cichon     GCCSSYPPTK GGGLGPCGKC QEGLEGGASG ASEPSEEVNK ASGPRACPPS
Rat        GCCSSHLPAR EGDPGPCRKC QDSPEGSSSG PGESSEERNK A.GSRASPPS
Mouse      GCCSSHLPAR EGDLGPCRKC QDSPEGGSSG PGESSEERNK A.DSRACPPS
```

FIG. 1E

```
              401                                                   450
              |                                                       |
Human         HHTKLKKTWL TRHSEQFECP RGCPEVEERP VARLRALKRA GSPEVQGAMG
Ahmad         HHTKLKKTWL TRHSEQFECP RGCPEVEERP VARLRALKRA GSPEVQGAMG
Cichon        HHTKLKKTWL TRHSEQFECP RGCPEVEERP VARLRALKRA GSPEVQGAMG
Rat           HHTKLKKTWL TRHSEQFECP GGCPGKGESP ATGLRALKRA GSPEVQGA.R
Mouse         HHTKLKKTWL TRHSEQFECP GGCSGKEESS ATGLRALKRA GSPEVQGASR

              451                                                   500
              |                      *                                |
Human         SPAPKRPPDP FPGTAEQGAG GWQEVRDTSI GNKDVDSGQH DEQKGPQDGQ
Ahmad         SPAPKRPPDP FPGTAEQGAG GLQEVRDTSI GNKDVDSGQH DEQKGPQDGQ
Cichon        SPAPKRPPDP FPGTAEQGAG GWQEVRDTSI GNKDVDSGQH DEQKGPQDGQ
Rat           GPAPKRPSHT FPGTGRQGAR AWQETPETST GSKA.EAQQQ EEQRGPRDGR
Mouse         GPAPKRPSHP FPGTGRQGAR AWQETPETII GSKA.EAEQQ EEQRGPRDGR
```

FIG. 1F

```
           501                                                    550
           |               *                                        |
Human      ASLQDPGLQD IPCLLLPAKL AQCQSCAQAA GEGGGHACHS QQVRRSPLGG
Ahmad      ASLQDPGLQD IPCLALPAKL AQCQSCAQAA GEGGGHACHS QQVRRSPLGG
Cichon     ASLQDPGLQD IPCLALPAKL AQCQSCAQAA GEGGGHACHS QQVRRSPLGG
Rat        IRLRESRLED TSCQHHLAGV TQCPSCVQAA GEVEILTSHS QKSHKLPLEE
Mouse      IRLQESRLVD TSCQHHLAGV TQCQSCVQAA GEVGVLTGHS QKSRRSPLEE

           551                                                    600
           |                                                    *   |
Human      ELQQEEDTAT NSSSEEGPGS GPDSRLSTGL AKHLLSGLGD RLCRLLRRER
Ahmad      ELQQEEDTAT NSSSEEGPGS GPDSRLSTGL AKHLLSGLGD RLCRLLRGER
Cichon     ELQQEEDTAT NSSSEEGPGS GPDSRLSTGL AKHLLSGLGD RLCRLLRRER
Rat        KPL.EEDSCA .TSEEGGGS. SPEASINKGL AKHLLSGLGD RLCRLLRKER
Mouse      KQLEEEDSSA .TSEEGGGGP GPEASLNKGL AKHLLSGLGD RLCRLLRKER
```

FIG. 1G

```
           601                                                650
           |         *          *                               |
Human      EALAWAQREG QGPAVTGDSP GIPRCCSRCH HGLFNTHWRC PRCSHRLCVA
Ahmad      EALAWAQRES QGPAVTEDSP GIPRCCSRCH HGLFNTHWRC PRCSHRLCVA
Cichon     EALAWAQREG QGPAVTEDSP GIPRCCSRCH HGLFNTHWRC PRCSHRLCVA
Rat        EALAWAQREG QGPAMTEDSP GIPHCCSRCH HGLFNTHWRC SHCSHRLCVA
Mouse      EALAWAQREG QGPAMTEDSP GIPHCCSRCH HGLFNTHWRC SHCSHRLCVA

           651                                                700
           |                                                  |
Human      CGRVAGTGRA REKAGFQEQS AEECTQEAGH AACSLMLTQF VSSQALAELS
Ahmad      CGRVAGTGRA REKAGFQEQS AEECTQEAGH AACSLMLTQF VSSQALAELS
Cichon     CGRVAGTGRA REKAGFQEQS AEECTQEAGH AACSLMLTQF VSSQALAELS
Rat        CGRIAGAGKN REKTGSREQR TDDCAQEAGH AACSLILTQF VSSQALAELS
Mouse      CGRIAGAGKN REKTGSQEQH TDDCAQEAGH AACSLILTQF VSSQALAELS
```

FIG. 1H

```
           701                                                    750
           |                                                        |
Human      TAMHQVWVKF DIRGHCPCQA DARVWAPGDA GQQKESTQKT PPTPQPSCNG
Ahmad      TAMHQVWVKF DIRGHCPCQA DARVWAPGDA GQQKESTQKT PPTPQPSCNG
Cichon     TAMHQVWVKF DIRGHCPCQA DARVWAPGDA GQQKESTQKT PPTPQPSCNG
Rat        TVMHQVWAKF DIRGHCFCQV DARVWAPGDG GQQKEPTEKT PPAPQLSCNG
Mouse      TVMHQVWAKF DIRGHCFCQV DARVWAPGDG GQQKEPTEKT PPTPQPSCNG

           751                                                    800
           |                                                        *
Human      DTHRTKSIKE ETPDSAETPA EDRAGRGPLP CPSLCELLAS TAVKLCLGHE
Ahmad      DTHRTKSIKE ETPDSAETPA EDRAGRGPLP CPSLCELLAS TAVKLCLGHD
Cichon     DTHRTKSIKE ETPDSAETPA EDRAGRGPLP CPSLCELLAS TAVKLCLGHE
Rat        DSNRTKDIKE ETPDSTESPA EDRAGRSPLP CPSLCELLAS TAVKLCLGHE
Mouse      DSNRTKDIKE ETPDSTESPA EDGAGRSPLP CPSLCELLAS TAVKLCLGHD
```

FIG. 1I

| | 801 | | | | 850 |
|---|---|---|---|---|---|
| Human | RIHMAFAPVT | PALPSDDRIT | NILDSIIAQV | VERKIQEKAL | GPGLRAGPGL |
| Ahmad | RIHMAFAPVT | PALPSDDRIT | NILDSIIAQV | VERKIQEKAL | GPGLRAGPGL |
| Cichon | RIHMAFAPVT | PALPSDDRIT | NILDSIIAQV | VERKIQEKAL | GPGLRAGPGL |
| Rat | RIHMAFAPVT | PALPSDDRIT | NILDSIIAQV | VERKIQEKAL | GPGLRAGSGL |
| Mouse | RIHMAFAPVT | PALPSDDRIT | NILDSIIAQV | VERKIQEKAL | GPGLRAGSGL |

| | 851 | | | | 900 |
|---|---|---|---|---|---|
| Human | RKGLGLPLSP | VRPRLPPPGA | LLWLQEPQPC | PRRGFHLFQE | HWRQGQPVLV |
| Ahmad | RKGLGLPLSP | VRPRLPPPGA | LLWLQEPQPC | PRRGFHLFQE | HWRQGQPVLV |
| Cichon | RKGLGLPLSP | VRPRLPPPGA | LLWLQEPQPC | PRRGFHLFQE | HWRQGQPVLV |
| Rat | RKGLSLPLSP | VRTQLSPPGA | LLWLQEPR.. | PKHGFRLFQE | HWRQGQPVLV |
| Mouse | RKGLSLPLSP | VRTRLSPPGA | LLWLQEPR.. | PKHGFHLFQE | HWRQGQPVLV |

FIG. 1J

```
              901                                                     950
              |                                      *                  |
Human         SGIQRTLQGN LWGTEALGAL GGQVQALSPL GPPQPSSLGS TTFWEGFSWP
Ahmad         SGIQRTLQGN LWGTEALGAL GGQVQALSPL APPQPSSLGS TTFWEGFSWP
Cichon        SGIQRTLQGN LWGTEALGAL GGQVQALSPL GPPQPSSLGS TTFWEGFSWP
Rat           SGIQKTLRLS LWGMEALGTL GGQVQTLTAL GPPQPTSLDS TAFWKGFSHP
Mouse         SGIQKTLRLS LWGMEALGTL GGQVQTLTAL GPPQPTNLDS TAFWEGFSHP

              951                                                    1000
              |                *                                        |
Human         ELRPKSDEGS VLLLHRALGD EDTSRVENLA ASLPLPEYCA LHGKLNLASY
Ahmad         ELRPKSDEGS VLLLHRAFGD EDTSRVENLA ASLPLPEYCA LHGKLNLASY
Cichon        ELRPKSDEGS VLLLHRALGD EDTSRVENLA ASLPLPEYCA LHGKLNLASY
Rat           EARPKLDEGS VLLLHRPLGD KDESRVENLA SSLPLPEYCA HQGKLNLASY
Mouse         ETRPKLDEGS VLLLHRTLGD KDASRVQNLA SSLPLPEYCA HQGKLNLASY
```

FIG. 1K

```
        1001                                                1050
        |                                                 * |
Human   LPPGLALRPL EPQLWAAYGV SPHRGHLGTK NLCVEVADLV SILVHADTPL
Ahmad   LPPGLALRPL EPQLWAAYGV SPHRGHLGTK NLCVEVADLV SILVHARTPL
Cichon  LPPGLALRPL EPQLWAAYGV SPHRGHLGTK NLCVEVADLV SILVHADTPL
Rat     LPLGLTLHPL EPQLWAAYGV NSHRGHLGTK NLCVEVSDLI SILVHAEAQL
Mouse   LPLGLTLHPL EPQLWAAYGV NSHRGHLGTK NLCVEVSDLI SILVHAEAQL

        1051                                                1100
        |   *                                               |
Human   PAWHRAQKDF LSGLDGEGLW SPGSQVSTVW HVFRAQDAQR IRRFLQMVCP
Ahmad   PAWHEAQKDF LSGLDGEGLW SPGSQVSTVW HVFRAQDAQR IRRFLQMVCP
Cichon  PAWHRAQKDF LSGLDGEGLW SPGSQVSTVW HVFRAQDAQR IRRFLQMVCP
Rat     PPWYRAQKDF LSGLDGEGLW SPGSQTSTVW HVFRAQDAQR IRRFLQMVCP
Mouse   PPWYRAQKDF LSGLDGEGLW SPGSQTSTVW HVFRAQDAQR IRRFLQMVCP
```

FIG. 1L

```
            1101                                                  1150
            |                                                        |
Human       AGAGALEPGA PGSCYLDAGL RRRLREEWGV SCWTLLQAPG EAVLVPAGAP
Ahmad       AGAGALEPGA PGSCYLDAGL RRRLREEWGV SCWTLLQAPG EAVLVPAGAP
Cichon      AGAGALEPGA PGSCYLDAGL RRRLREEWGV SCWTLLQAPG EAVLVPAGAP
Rat         AGAGTLEPGA PGSCYLDSGL RRRLREEWGV SCWTLLQAPG EAVLVPAGAP
Mouse       AGAGTLEPGA PGSCYLDAGL RRRLREEWGV SCWTLLQAPG EAVLVPAGAP

            1151                                                  1200
            |                                      *                 |
Human       HQVQGLVSTV SVTQHFLSPE TSALSAQLCH QGPSLPPDCH LLYAQMDWAV
Ahmad       HQVQGLVSTV SVTQHFLSPE TSALSAQLCH QGASLPPDCH LLYAQMDWAV
Cichon      HQVQGLVSTV SVTQHFLSPE TSALSAQLCH QGPSLPPDCH LLYAQMDWAV
Rat         HQVQGLVSTI SVTQHFLSPE TSALSAQLCH QGASLPPDHR MLYAQMDRAV
Mouse       HQVQGLVSTI SVTQHFLSPE TSALSAQLYH QGASLPPDHR MLYAQMDRAV
```

FIG. 1M

```
         1201            1215
         |                  |
Human    FQAVKVAVGT LQEAK
Ahmad    FQAVKVAVGT LQEAK
Cichon   FQAVKVAVGT LQEAK
Rat      FQAVKVAVGT LQEAK
Mouse    FQAVKAAVGA LQEAK
```

HUMAN HAIRLESS GENE AND PROTEIN

CROSS-REFERENCE TO RELATED APPLICATIONS

This application is a divisional of U.S. Ser. No. 09/287,354, filed Apr. 7, 1999, now U.S. Pat. No. 6,348,348, which claims benefit of U.S. Provisional Ser. No. 60/080,888, filed Apr. 7, 1998, the entire disclosures of which are incorporated herein by reference.

STATEMENT REGARDING SPONSORED RESEARCH OR DEVELOPMENT

The invention described herein was made in the course of work under grant number DK-46074 from the National Institutes of Health. The U.S. government may retain certain rights in this invention.

BACKGROUND OF THE INVENTION

1. Field of Invention

The present invention pertains to products and processes useful in the fields of development, genetics, and transcription biochemistry. The invention is generally useful in the diagnosis and treatment of dermatologic conditions.

2. Description of the Related Art

Although hair loss is a problem of great interest to dermatologists and the lay public, basic knowledge of the biology of hair growth and maintenance has been limited.

In most mammals, hair does not grow continuously but undergoes cycles of activity involving periods of growth, rest, and shedding. On the human scalp, from 100,000 to 350,000 hair fibers or shafts undergo metamorphosis in three distinct stages:

(a) the growth phase (anagen) during which the hair root bulb or dermal papilla (also called the "follicular papilla") penetrates deep into the dermis with the cells of the bulb dividing rapidly and differentiating in the process of synthesizing keratin, the substance of the hair shaft itself. In normal humans, this growth phase is thought to last from one to five years;

(b) the transitional phase (catagen) is marked by the cessation of mitosis and lasts from two to three weeks; and (c) the resting phase (telogen) where the hair is retained within the scalp for up to 12 weeks before the emerging new hair developing below it dislodges the telogen-stage shaft from its follicle.

Experiments with mouse hair follicles showed that the anagen-stage stem cells, stored within the bulge area of the follicle, proliferate during early anagen and migrate to the root bulb region prior to differentiation. See U.S. Pat. No. 5,279,969. The bulge cells can be stimulated to proliferate in response to physical and chemical stimuli causing telogen follicles to commence anagen. In addition, the physical proximity of the follicular papilla to the stem cell-containing bulge area plays a role in the onset of the anagen stage. It has been speculated that damage to the bulge region results in permanent alopecia, whereas damage to the hair root bulb alone results in alopecia areata and is temporary.

It is generally accepted that genetic hair loss arises from activation of an inherited sensitivity to circulating androgenic hormones. Such androgenic alopecia is the single most common type of recognizable alopecia to affect both men (50%) and women (30%), primarily of Caucasian origin. Gradual changes in the width and length of the hair shaft are experienced over time and with increasing age, prematurely in some. Terminal hair is gradually converted to short, wispy, colorless vellus hair. As a consequence, men in their 20's and women in their 30's and 40's begin to notice their hair becoming finer and shorter. In addition, the ratio of growing hairs to hairs in the resting and shedding phases declines from as high as 9:1 to as low as 2:1.

Androgenic alopecia, or male pattern baldness, is largely the result of heredity, advancing age, and male hormone secretion, specifically the hormone dihydrotestosterone (DHT). At advanced stages, male pattern baldness is characterized by a bald scalp at the crown of the head and a horseshoe shaped fringe of hair remaining on the sides of the head. Male pattern baldness may be mediated by time-dependent, steroid hormone-regulated gene expression that results in a diminution in the growing phase of scalp hair.

Minoxidil, a potent anti-hypertensive medication, has been used with limited success to treat male pattern baldness by topical application to the scalp. See U.S. Pat. Nos. 4,139,619 and 4,596,812. A 2% or 5% solution containing alcohol and polyethylene glycol is used. One theory for its mode of action is that blood vessels are dilated and the increased blood supply stimulates nourishment of hair follicles. Many patients, however, do not achieve a satisfactory result (younger patients and patients with less hair loss have better results), the degree of new hair growth is usually minimal, and the area of the scalp that is affected is usually limited to the vertex cranii. Minoxidil's effectiveness for the treatment of androgenic alopecia may be limited because it does not reduce production of the hormones responsible for causing male pattern baldness.

Therefore, another approach for treating male pattern baldness has been the administration of agents which inhibit the conversion of testosterone to DHT. Testosterone binds specifically to the 5 alpha-reductase enzyme which converts testosterone to its active metabolite DHT. In turn, DHT binds to nuclear receptor proteins and may regulate the synthesis of specific proteins which lead to male pattern baldness.

An orally administered inhibitor of 5 alpha-reductase currently prescribed for the treatment of male pattern baldness is finasteride, a synthetic 4-azasteroid compound. See U.S. Pat. Nos. 4,377,584; 4,760,071; 5,547,957; and 5,571,817. Finasteride is more conveniently administered than minoxidil and is more effective than minoxidil in treating androgenic alopecia. However, finasteride also has undesirable effects which include reducing libido, erection, and semen volume in men; and causing fetal defects in pregnant women.

A genetic approach to developing pharmaceutical candidates is to screen small molecules for modulation of transcription factor activity which regulates hair growth and/or maintenance. For example, Tularik has described high-throughput assays for screening candidate chemical agents which modulate transcription mediated by sequence-specific transcription factors. But a human transcription factor essential to the growth and/or maintenance of hair was not available until the invention described in the present application.

For all of the above reasons, it was necessary to develop molecular probes and genetic models for hair loss. In hr/hr (hairless) mutant mice, initial hair growth is normal but, after the first wave of shedding, hair fails to grow back and complete loss of hair results. In this respect, the development of hair loss resembles alopecia universalis caused by a rare inherited mutation in humans (see Ahmad et al., Science, 279, 720–724, 1998; Cichon et al., Hum. Mol. Genet., 7, 1671–1679 and 1987–1988, 1998). In addition, mutant mice show increased sensitivity to ultraviolet (UV)

radiation and chemical-induced skin carcinogenesis. The human Hairless gene is identified and characterized herein.

SUMMARY OF THE INVENTION

The invention provides isolated polynucleotides corresponding to the human Hairless (HR) gene and their nucleotide sequences, isolated polypeptides and amino acid sequences of the Hairless (Hr) protein, and fragments thereof.

These products may be used in processes to detect Hairless gene or protein expression, to inhibit Hairless gene or protein expression, to isolate Hairless polynucleotide or polypeptide from a crude mixture, to produce Hairless polypeptide, to identify a binding molecule specific for Hairless, to isolate the specific binding molecule from a crude mixture, to detect the specific binding molecule in a crude mixture, to identify an agent which specifically binds Hairless, to isolate the specific binding agent from a crude mixture, to detect the specific binding agent in a crude mixture, to transfect a host cell, and to produce a non-human transgenic animal.

The present invention is also directed to screening methods to identify agents that affect expression of the human HR gene or transcriptional activity of the human Hr protein.

Uses of Hairless polynucleotide, polypeptide, and specific binding molecule are further described below. Kits comprising the aforementioned products are also provided to practice the described processes; such kits would further comprise instructions for performing the processes and/or standards to calibrate diagnostic assays and/or other reagents to perform the processes.

BRIEF DESCRIPTION OF THE DRAWING

FIGS. 1A–1M show a comparison of the amino acid sequences of the present invention (Hum Hr, SEQ ID NO:2); a human sequence (accession number AFO39196, SEQ ID NO:3) published by Ahmad et al. (Science, 279, 720–724, 1998); a human sequence (accession number not available, SEQ ID NO:4) published by Cichon et al. (Hum. Mol. Genet., 7, 1671–1679 and erratum at 1987–1988, 1998); a rat sequence (accession number U71293, SEQ ID NO:5) published by Thompson (J. Neurosci., 16, 7832–7840, 1996); and a mouse sequence (accession number Z32675, SEQ ID NO:6) published by Cachon-Gonzalez et al. (Proc. Natl. Acad. Sci. USA, 91, 7717–7721, 1994). An asterisk indicates a position at which there is a difference among the human sequences.

DESCRIPTION OF PREFERRED EMBODIMENTS

This invention is based on the discovery of a polynucleotide which encodes a homolog of the mouse hairless gene. Polynucleotides and polypeptides of the present invention represent molecules which could be detected diagnostically or targeted therapeutically in vitro, ex vivo, or in vivo. These polynucleotides and their predicted translation products are unique as compared to nucleotide and amino acid sequences, respectively, which are known in the prior art.

According to one aspect of invention, a complementary DNA sequence (cDNA) representing an about 5 Kb messenger RNA (mRNA) transcript in human cells may be monitored by polynucleotide detection techniques. Nucleotide sequence specific for Hairless can be used as a probe. Such probes could be full length covering the entire transcribed message or gene, at least one coding region, or a shorter length fragment which is unique to the Hairless transcript or gene but contains only a portion of same. The polynucleotide may be at least 20 bases to 500K bases long (e.g., 20, 30, 50, 100, 250, 500, 1000, 2500, 5000, 10 K, 20 K, 40 K, 100K, 250K, or 500K bases).

The Sanger and Maxam-Gilbert sequencing reactions produce a collection of polynucleotide fragments by enzymatic and chemical methods, respectively. These fragments may be separated by electrophoresis as a ladder of bands with different mobilities, detected by labeling, and isolated by by collecting the moving zone containing the desired fragment with a relative mobility predicted from comparison to a standard. In contrast to template-dependent extension and limited hydrolysis, polynucleotide fragments may be produced by limited or complete nuclease digestion. Caruthers' phosphoramidite synthesis may also be used to produce short oligonucleotides. Chromatography and mass spectroscopy are alternative methods of separation and detection, respectively.

The polypeptide of the invention has an amino acid sequence which may be predicted from the nucleotide sequence of the aforementioned polynucleotide. Full length polypeptide or a shorter length polypeptide fragment can be produced with the predicted amino acid sequence. The length of the polypeptide may be in the range of 5 residues to 1250 residues (e.g., at least 10, 25, 50, 75, 100, 250, 500, 750 or 1000 residues). Translation of the aforementioned polynucleotide fragments may be used to produce any desired polypeptide fragment. Edman degradation produces a series of polypeptide fragments which are separated during amino acid sequencing. Fragments may also be produced by chemical or proteolytic hydrolysis. Short oligopeptides may be chemically synthesized by Merrifield's method. Polypeptides may be separated by electrophoresis, velocity sedimentation, or chromatography; they may be detected by labeling, their spectra of a radiated or adsorbed electromagnetic wave, or mass spectroscopy.

Related nucleotide or amino acid sequences are found when there is similarity or identity of sequence and this may be determined by comparison of sequence information, nucleotide or amino acid, or through hybridization between a human Hairless probe and a candidate source (e.g., Southern or Northern blots, genomic or cDNA libraries). Conservative changes, such as Glu/Asp, Val/Ile, Ser/Thr, Arg/Lys and Gln/Asn may also be considered in determining sequence similarity.

Typically, a nucleotide sequence may show as little as 80% sequence identity, and more preferably at least 90% sequence identity, between the target sequence and the human Hairless polynucleotide excluding any deletions or additions which may be present, and still be considered related. Nucleotide sequence identity may be at least 95% and, most preferably, nucleotide sequence identity is at least 98%. Amino acid sequences are considered to be related with as little as 90% sequence identity between the two polypeptides; however, 95% or greater sequence identity is preferred and 98% or greater sequence identity is most preferred.

Hairless is well conserved between rodents and man. Thus, the use of complex mathematical algorithms is not required because amino acid sequences can be aligned without introducing many gaps. But such algorithms are known in the art, and implemented using default parameters in commercial software packages provided by DNASTAR, Genetics Computer Group, Hitachi Genetics Systems, and Oxford Molecular Group (formerly Intelligenetics). See Doolittle, *Of URFS and ORFS*, University Science Books, 1986; Gribskov and Devereux, *Sequence Analysis Primer*, Stockton Press, 1991; and references cited therein. Percentage identity between a pair of sequences may be calculated by the algorithm implemented in the BESTFIT computer program (Smith and Waterman, J. Mol. Biol., 147, 195–197, 1981; Pearson, Genomics, 11, 635–650, 1991). Another algorithm that calculates sequence divergence has been adapted for rapid database searching and implemented in the BLAST computer program (Altschul et al., Nucl. Acids Res., 25, 3389–3402, 1997).

Conservative amino acid substitutions, such as Glu/Asp, Val/Ile, Ser/Thr, Arg/Lys and Gln/Asn, may also be considered when making comparisons because the chemical similarity of these pairs of amino acid residues would be expected to result in functional equivalency. Amino acid substitutions that are expected to conserve the biological function of the native Hairless polypeptide would conserve chemical attributes of the substituted amino acid residues such as hydrophobicity, hydrophilicity, side-chain charge, or size. Functional equivalency or conservation of biological function may be evaluated by methods for structural determination and bioassay as disclosed herein. Thus, amino acid sequences are considered to be related with as little as 90% sequence similarity between the two polypeptides; however, 95% or greater sequence similarity is preferred and 98% or greater sequence similarity is most preferred.

The codons used in the native nucleotide sequences may be adapted for translation in a heterologous host by adopting the codon preferences of the host. This would accommodate the translational machinery of the heterologous host without a substantial change in the chemical structure of the polypeptide.

While the rat and mouse Hairless sequences may be used as a source for making variant human polynucleotides and polypeptides, the full length rat and mouse Hairless sequences are not within the scope of the present invention.

A recombinant clone or expression construct containing a Hairless nucleotide sequence is a preferred form of the polynucleotide of the present invention. The recombinant clone or expression clone may be an episome, phagemid, plasmid, bacteriophage, cosmid, yeast artificial chromosome (YAC), or bacterial artificial chromosome (BAC). Such clone or construct could be single- or double-stranded; nucleotides may be deoxyribonucleosides, ribonucleosides, nucleosides with a modified base, nucleotides with a modified ribose, or combinations thereof; linkages between nucleotides may be comprised of phosphorus, nitrogen, sulfur, oxygen, carbon, or combinations thereof.

The expression construct is further comprised of a regulatory region for gene expression (e.g., promoter, enhancer, silencer, splice donor and acceptor sites, polyadenylation signal, cellular localization sequence) and, optionally, an origin of replication that allows chromosomal or episomal replication in a selected host cell. The expression construct may be based on a general-purpose vector with at least on regulatory region from a mammalian gene (e.g., actin, hormone responsive element of glucocorticoid receptor, histone, metallothionein) or a virus (e.g., adenovirus, baculovirus, cytomegalovirus, herpes virus, Moloney leukemia virus, mouse mammary tumor virus, Rous sarcoma virus, SV40 virus), as well as regions suitable for genetic manipulation (e.g., selectable marker, linker with multiple recognition sites for restriction endonucleases, promoter for in vitro transcription, primer annealing sites for in vitro replication, recognition site mediating site-specific recombination). The advantages of such clones or constructs may include ease of genetic manipulation, a source of replicated copies, and the ability to shuttle between different host cells or organisms.

Production of such vectors and constructs, like any recombinant molecule, are known in the art and typically involves enzymes, such as Taq polymerase, DNA and RNA polymerases, DNA and RNA ligases, restriction endonucleases, S1 nuclease, reverse transcriptase, and ribonuclease H. See Kornberg and Baker, *DNA Replication*, Freeman, 1991. The recombinant molecule may be transfected into a host, selected positively or negatively, and further manipulated.

Vectors, reagents, and other supplies are commercially available. See, for example, the catalogs and product information of Amersham Pharmacia Biotech, Bio101, Bio-Rad, CLONTECH, Invitrogen, Molecular Probes, New England Biolabs, Novagen, PharMingen, Pierce Chemical, Promega, Roche Molecular Biochemicals, Sigma-Aldrich, Stratagene, and United States Biological.

A heterologous promoter may be especially useful to regulate expression in a host cell or transgenic animal. See No et al., (Proc. Natl. Acad. Sci. USA, 93, 3346–3351, 1996); Rivera et al. (Nat. Med., 2,1028–1032,1996); Allgood and Eastman (Curr. Opin. Biotechnol., 8, 474–479, 1997); U.S. Pat. Nos. 5,589,362; 5,650,298; and 5,654,168.

The invention also provides primer pairs and other polynucleotides for use in amplifying polynucleotides (e.g., polymerase chain reaction or PCR, ligation chain reaction or LCR, transcription-mediated amplification or TMA, other thermal cycling or isothermal reactions) and hybridization probes. A set of such primers may be selected and used for PCR assays to quantitate Hairless transcript abundance within cells. Oligonucleotide sequences may be selected using methods such as those described in U.S. Pat. Nos. 5,556,749 and 5,639,612, or others known to the skilled artisan. Therefore, this invention will be useful for development and utilization of Hairless primers and other polynucleotides to quantitate cognate RNA and DNA within cells. This information may then be used to correlate hair growth/loss with Hairless expression or Hairless-regulated transcription. Primers that specifically amplify sequences in the vicinity of the Hairless genetic locus also serve as a sequence tagged site (STS) for 8p 12–21.

A host cell may be transfected with an expression construct comprised of the polynucleotide of the invention. The host cell may be a human cell line, bacterium, yeast, insect cell, plant cell, rodent cell, cell in a primary culture, established cell line, somatic cell, or stem cell (e.g., fibroblast, neuron, glial). This invention also provides Hairless transgenic non-human animals and mutants (e.g., site-directed mutations of the human Hairless gene) thereof, and mutants of human somatic cells by using the polynucleotides of the invention. Preferably, the transfected cell or transgenic animal will express the human Hairless gene or a variant thereof. A cell or organism without a Hairless gene (e.g., null mutant, gene knockout) is a preferred host for introduction of the human Hairless gene or a variant thereof because results of functional assays will not be confounded by endogenous Hairless activity.

Based on the Hairless nucleotide sequences, a specific binding molecule (e.g., antisense oligonucleotide or ribozyme) can be used to inhibit Hairless gene expression in an organism. Alternatively, specific binding molecules developed to neutralize the Hairless protein activity may be produced in or administered to an organism. Algorithms to guide the selection of hybridization probes, oligonucleotide primers, polypeptide binding molecules, and antigenic peptides have also been implemented in computer software packages.

This invention provides isolated polypeptide having biological activity of Hairless and a method for preparation of such polypeptides. The residues of the polypeptide may be natural amino acids, designer amino acids, or non-classical amino acids of either the D or L optical isomer; the residues may be modified by acylation, glycosylation, methylation, phosphorylation, sulfation, or combinations thereof; and linkages between residues may be comprised of phosphorus, nitrogen, sulfur, oxygen, carbon, or combinations thereof. The amino acid sequence of Hairless antigen can be used for preparation of specific binding molecules (e.g., polyclonal or monoclonal antibody, antibody fragment, humanized antibody, single chain antibody, phage hybrid protein or other members of a combinatorial library) for monitoring protein expression, affinity purification, and functional studies.

Antibody may be produced by immunizing an animal (e.g., chicken, goat, hamster, horse, mouse, rabbit, rat) with Hairless antigen. The immune response may be potentiated by immunoadjuvant, conjugation of antigen to a multivalent carrier, booster immunization, or combinations thereof. Antibody fragments may be prepared by proteolytic cleavage or genetic engineering; humanized antibody and single chain antibody may be prepared by transplanting sequences from the antigen binding regions of antibodies to framework molecules. Specific binding molecules may also be generally produced by screening a combinatorial library for a clone which specifically binds Hairless antigen (e.g., phage display library). See U.S. Pat. Nos. 5,403,484; 5,723,286; 5,733,743; 5,747,334; and 5,871,974. Antigen may be full length Hairless polypeptide or at least one fragment thereof.

For immunological screening methods, antibody preparations, either monoclonal or polyclonal, may be utilized. Polyclonal antibodies, although generally less specific, typically are more useful in gene isolation. Immunizing an animal may produce polyclonal antibody which recognizes multiple epitopes of the Hairless antigen or at least one immunodominant epitope. Monoclonal antibody may be produced by fusing lymphocytes of an immunized animal with a myeloma or other immortalized cell, and selecting clones producing antibody that recognizes a desired Hairless epitope or possesses a desired properties (e.g., activating or neutralizing an activity of Hairless polypeptide, precipitating Hairless polypeptide or a fragment thereof). The epitope bound by the antibody may be present in the native Hairless polypeptide or only in a denatured form of Hairless.

A molecule able to specifically hybridize to a polynucleotide of the invention (e.g., a complementary polynucleotide) is also considered a specific binding molecule. Hybridization conditions are preferably chosen with a stringency that uniquely identifies the human Hairless gene in a population of genomic DNA or the human Hairless transcript in a population of cellular RNA. Conditions may also be chosen to distinguish human Hairless nucleotide sequences from those of other species by a physical criterion like sedimentation velocity or electrophoretic mobility. Alternatively, hybridization conditions may be relaxed to identify orthologs or paralogs in human or other mammalian species. Specific hybridization by such a molecule is also useful for monitoring gene expression, genetic profiling and fingerprinting, and functional studies.

The specific binding molecule of the invention may be a chemical mimetic; for example, an aptamer or peptidomimetic. It is preferably a short oligomer selected for binding affinity and bioavailability (e.g., passage across the plasma and nuclear membranes, resistance to hydrolysis of oligomeric linkages, adsorbance into cellular tissue, and resistance to metabolic breakdown). The chemical mimetic may be chemically synthesized with at least one non-natural analog of a nucleoside or amino acid (e.g., modified base or ribose, designer or non-classical amino acid, D or L optical isomer). Modification may also take the form of acylation, glycosylation, methylation, phosphorylation, sulfation, or combinations thereof. Oligomeric linkages may be phosphodiester or peptide bonds; linkages comprised of a phosphorus, nitrogen, sulfur, oxygen, or carbon atom (e.g., phosphorothionate, disulfide, lactam, or lactone bond); or combinations thereof. The chemical mimetic may have significant secondary structure (e.g., a ribozyme) or be constrained (e.g., a cyclic peptide). Solid-phase synthesis is preferred to avoid representational bias and to generate chemical diversity in making a library of non-natural mimetics. See, for example, U.S. Pat. Nos. 5,650,489 and 5,877,030. Cleavage from the solid support would produce a solution library or selectively release/retain the mimetic.

For detection, the antibody is labeled using radioactivity or any one of a variety of second antibody/enzyme conjugate systems that are commercially available (e.g., alkaline phosphatase, β-galactosidase, horseradish peroxidase). Chemical staining may be used to detect polynucleotide (e.g., acridine orange, ethidium bromide) or polypeptide (e.g., amido black, coomassie brilliant blue) of the invention. Typically, polynucleotide, polypeptides, and specific binding molecule are labeled for use as probes in assays of the invention. Preferably the probe is labeled with a small molecule (e.g., biotin, chromochrome, colloidal gold, digoxygenin, dinitrophenol, fluorochrome, radioisotope, spin label), although enzymes (e.g., alkaline phosphatase, β-galactosidase, peroxidase) or other methods (e.g., agglutination, chemiluminescence, electron spin resonance, energy transfer, flocculation, nuclear magnetic resonance, spectroscopy, surface plasmon resonance) may be used to detect the probe.

Biological functions or activities of Hairless include, but are not limited to, transcription, growth and maintenance of hair, resistance to UV radiation and chemical-induced skin carcinogenesis, neural development, neurological or behavioral characteristics, and other effects of thyroid hormone mediated through Hairless.

Modulation of gene expression may be effected by affecting transcriptional initiation, transcript stability, translation of the transcript into protein product, protein stability, or combinations thereof. Quantitative effects can be measured by conventional techniques such as in vitro transcription, in vitro translation, Northern hybridization, polynucleotide hybridization, reverse transcription-polymerase chain reaction (RT-PCR), run-on transcription, solution hybridization, nuclease protection, Southern hybridization, cell surface protein labeling, metabolic protein labeling, antibody binding, enzyme linked immunosorbent assay (ELISA), immunofluorescence, immunoprecipitation (IP), fluorescence activated cell analysis (FACS), radioimmunoassay (RIA), and western blotting.

Gene expression is conveniently assayed by use of a reporter or selectable marker gene whose protein product is easily assayed. Such reporter genes include alkaline phosphatase, β-galactosidase (LacZ), chloramphenicol acetyltransferase (CAT), β-glucoronidase (GUS), green fluorescent protein (GFP), β-lactamase, luciferase (LUC), or derivatives thereof. Such reporter genes would use cognate substrates that are preferably assayed by a chromogen, fluorescent, or luminescent signal. Alternatively, the assayed product may be tagged with a heterologous polypeptide epitope (e.g., FLAG, MYC, SV40 T antigen, glutathione-S-transferase or GST, hexahistidine, maltose binding protein or MBP) for which cognate antibodies or affinity resins are commercially available. Examples of drugs for which selectable marker genes exist are ampicillin, hygromycin, kanamycin/neomycin, puromycin, and tetracycline. A metabolic enzyme (e.g., dihydrofolate reductase, thymidine kinase) may be used as a selectable marker in sensitive host cells or auxotrophs.

It is a particular object of the invention to provide processes for screening candidate chemical agents for the ability to modulate expression of the HR gene and/or activity of the Hr protein. It is another object of the invention to provide reporter constructs and expression systems for screening candidate chemical agents. Yet another object of the invention to provide processes for identifying candidate chemical agents to regulate the growth and/or maintenance of hair.

In such embodiments of the invention, a method is provided for screening candidate chemical agents for the ability to modulate hair development and/or cell differentiation by activating HR-regulated gene expression or by inhibiting HR-regulated gene expression. Moreover, a method is provided for screening candidate chemical agents for use in modulating maintenance and/or growth of hair. Furthermore, a method of screening candidate chemical agents which modulate the binding of Hr to thyroid hormone receptor is provided to regulate hairless transcriptional activity. A high-throughput screening assay is preferred.

A screening method may comprise administering a candidate chemical agent to an organism, or incubating a candidate chemical agent to a cell or tissues, and directly assaying for modulation of HR gene activity or Hr protein activity. Modulation may be an increase or decrease in activity. HR gene or Hr protein activity may be increased at the level of rate of transcript initiation, rate of transcript elongation, stability of transcript, translation of transcript, rate of translation initiation, rate of translation elongation, stability of protein, rate of protein folding, proportion of protein in active conformation, functional efficiency of protein (e.g., binding constant for DNA, activation or repression of transcription), or combinations thereof. See, for example, U.S. Pat. Nos. 5,071,773 and 5,262,300.

A screening method may comprise incubating a candidate chemical agent with a cell containing a reporter construct, the reporter construct comprising an Hr-responsive transcription regulatory region covalently linked in a cis configuration to a downstream gene encoding an assayable product; and measuring production of the assayable product. A candidate chemical agent which increases production of the assayable product would be identified as an agent which activates gene expression from the HR-responsive region, and a candidate chemical agent which decreases production of the assayable product would be identified as an agent which inhibits gene expression from the HR-responsive region. See, for example, U.S. Pat. Nos. 5,849,493 and 5,863,733.

A screening method may comprise measuring in vitro transcription from a reporter construct incubated with Hr protein (or transcriptionally active fragment thereof) in the presence or absence of a candidate chemical agent, the reporter construct comprising a transcription regulatory region which is responsive to Hr protein (or transcriptionally active fragment thereof); and determining whether transcription is altered by the presence of the candidate chemical agent. In vitro transcription is preferably assayed using a cell-free extract (more preferably, a nuclear extract); partially purified fractions of the cell-free extract; purified transcription factors or RNA polymerase; or combinations thereof. See U.S. Pat. Nos. 5,453,362; 5,534,410; 5,563,036; 5,637,686; 5,708,158; and 5,710,025.

A screening method may comprise incubating Hr protein (or fragment thereof) with a candidate chemical agent and thyroid hormone receptor (or fragment thereof); and determining the amount of the thyroid hormone receptor (or fragment thereof) which is bound to Hr protein (or fragment thereof), the desired chemical agent being one which increases or decreases binding. Preferably, at least one of the Hr protein (or fragment thereof) and the thyroid hormone receptor (or fragment thereof) is immobilized to a solid substrate to facilitate separation of bound from unbound complexes.

Methods for measuring transcriptional or translational activity in vivo can be any which are known. For example, a nuclear run-on assay may be employed to measure transcription of a reporter gene. The translation of the reporter gene may be measured by determining the activity of the translation product of the reporter gene. Methods for measuring the activity of an assayable product of certain reporter genes are well known.

In a preferred embodiment, the above methods are assayed in vitro with or without hairless transcription activity. This may be accomplished by using cell or proteins from sources without hairless transcription activity such as mouse hr/hr mutant cells or animals, gene knockout somatic cells or animals, or cells which do not normally express hairless. In another preferred embodiment, the transcription is assayed with or without thyroid hormone, thyroid hormone receptor, or at different stages of development or cell differentiation.

Candidate chemical agents can also be screened for use in regulating the growth and/or maintenance of hair by their ability to regulate the activity of Hr protein. The ability of a candidate chemical agent to regulate the transcriptional activity of Hr protein may be assessed by measuring transcription from an Hr-responsive regulatory region.

A transcription reaction comprises a regulatory region responsive to Hr protein and a reporter gene. The reporter gene operably linked to the regulatory region in a reporter construct could be any gene known in the art. In a preferred embodiment, the length of the promoter region to be assayed is less than 200 bp and no more than 1000 bp. The regulatory region in the reporter construct can be any polynucleotide to which Hr protein binds by itself or in a complex (e.g., with thyroid hormone receptor). The regulatory region is responsive to Hr protein which regulates transcription of the reporter gene downstream from and adjacent to the regulatory region. One possible example of such regulatory regions comprises the upstream sequence of the Hairless gene, especially sequences which are identified by a consensus thyroid hormone receptor binding site (see SEQ ID NOS:7–10). Other regulatory regions may be identified and isolated by selection according to sequence-specific binding of Hr protein. See U.S. Pat. Nos. 5,747,253; 5,869,241; and 5,888,738.

Suitable methods for measuring in vitro transcription are known. In vitro transcription may be carried out by incubating a reporter construct, labeled nucleotides (e.g., $^{32}$P-ATP), transcriptionally active cell-free extract, nucleotides, and buffer reagents in the presence and absence of a candidate chemical agent. The procedures for producing cell-free extracts and partially purified fractions are well-described in the art; the conditions for in vitro transcription are also well known. The labeled transcript can be separated by slab or capillary gel electrophoresis, detected by autoradiography, and quantitated by any technique known in the art. Optionally, in vitro transcription can be carried out in the presence of Hr protein and/or thyroid hormone receptor.

A candidate chemical agent which increases production of an assayable product in the cell indicates the potential to increase expression of the HR gene or a downstream target gene of the Hr protein. A candidate chemical agent which increases the level of in vitro transcription indicates its ability to enhance the activity of the transcription regulatory Hr protein. Candidate chemical agents which increase expression of the HR gene or its downstream target gene can potentiate the growth and/or maintenance of hair. These agents can potentially be administered to a human.

A candidate chemical agent which decreases production of assayable product in the cell indicates the potential for the agent to decrease expression of the HR gene or its downstream target gene. A candidate chemical agent which decreases the level of in vitro transcription indicates its ability to reduce the activity of the transcription regulatory Hr protein. Candidate chemical agents which decrease expression of the HR gene or its downstream target gene can inhibit the growth and/or maintenance of hair. These agents can potentially be administered to a human.

According to another embodiment of the invention, candidate chemical agents regulating the binding between Hr protein and thyroid hormone receptor may be identified. Hr protein can be attached to an insoluble polymeric support such as acrylamide, agarose, cellulose, or plastics, or other supports such as glass. A candidate chemical agent is incubated with the immobilized Hr protein in the presence of thyroid hormone receptor. Alternatively, thyroid hormone receptor can be immobilized on a solid support and a candidate chemical agent can be incubated with the immobilized thyroid hormone receptor in the presence of Hr protein. After incubation, non-binding components can be washed away, leaving thyroid hormone receptor bound to Hr protein/solid support or Hr protein bound to thyroid hormone receptor/solid support, respectively. Washing may be facilitated by forming the solid support into a bilious strip, a well of a 96-well plate, a bead, a chromatography column, or a porous membrane. Solution transfer may be accomplished by fluid channels, magnetic particles, or robotics.

The amount of HR protein or thyroid hormone receptor can be quantified by any means known in the art. For example, it can be determined using a binding assay detected by autoradiography, enzyme colorimetry, excitation energy transfer, fluorescence polarization, fluorescence quenching, liquid scintillation, or surface plasmon resonance. The amount of bound Hr protein or thyroid hormone receptor may be compared with and without the candidate chemical agent. A desirable agent is one which increases or decreases the binding of Hr protein to thyroid hormone receptor.

Although the binding of Hr protein and thyroid hormone receptor is described above, it should be understood that binding between Hr protein and another transcription factor (i.e., hetero-oligomers) or formation of Hr homo-oligomers may be assayed in a similar manner. A complex of Hr protein and ROR receptor may be formed, or Hr protein may form a complex with another orphan receptor. Such complexes may be formed and assayed in the presence or absence of ligand, with or without cognate nucleotide recognition sequence, or combinations thereof. Hr protein may not bind a nucleotide recognition sequence. However, sequence specificity may be changed or conferred by joining Hr protein to a heterologous DNA-binding domain (DBD) of known sequence specificity.

Bound complex may be visualized by X-ray crystallography or nuclear magnetic resonance spectroscopy to identify contact points between subunits of the oligomer. Small molecule mimetics can be designed to increase or decrease formation of oligomers. See U.S. Pat. Nos. 5,790,421 and 5,835,382.

The identification of other genes and proteins whose expression or activity is Hr-dependent will provide additional targets for drug development. Gene expression profiles may be compared prior to and after induction of HR transcription or Hr transcriptional activity. Transcription of Hr-dependent genes may be activated by addition of thyroid hormone (comparing with and without Hr activity), or by introducing the HR gene under the control of an inducible promoter into a host cell that lacks endogenous HR transcription.

Hr-dependent genes may be identified by techniques detecting differential expression such as a subtractive cDNA library screened with post-induction transcripts minus pre-induction transcripts, or by differential screening of cDNA or genomic clone libraries. Differential message display (U.S. Pat. Nos. 5,459,037; 5,599,672; 5,665,544; 5,707,807; 5,807,680; 5,814,445; 5,851,805; and 5,876,932); subtractive hybridization (U.S. Pat. Nos. 5,316,925; 5,643,761; 5,804,382; 5,830,662; 5,837,468; 5,846,721; and 5,853,991); computer-assisted comparison with an electronic database (e.g., U.S. Pat. No. 5,840,484); differential screening of arrayed cDNA clones or libraries (e.g., U.S. Pat. Nos. 4,981,783; 5,206,152; and 5,624,801); reciprocal subtraction differential display (RSDD; U.S. Pat. No. 5,882,874); and serial analysis of gene expression (SAGE; U.S. Pat. No. 5,866,330) may be used to identify Hr-dependent genes.

The Hr-dependent gene transcripts will be translated into Hr-dependent proteins, such proteins may be identified by comparing the pattern of proteins expressed prior to and after induction of Hr (with or without thyroid hormone). For example, pre- and post-induction cultures of the host cells may be $^{35}S$-pulsed, protein extracts may be made from whole cell lysates or subcellular fractions, and Hr-dependent proteins will be identified by their increased or decreased signal intensity in two-dimensional gels of $^{35}S$-labeled proteins from pre- and post-induction cultures. Proteins of interest (i.e., labeled proteins which increase or decrease in abundance) may be isolated, N-terminal or internal peptide amino acid sequence may be determined, and the Hr-dependent genes of interest identified by cloning with degenerate polynucleotides whose sequences are predicted according to the determined amino acid sequence.

Hr-dependent genes may also be identified by promoter trapping. Hr may be induced in cells after introducing the HR gene under the control of an inducible promoter into a host cell that lacks endogenous HR gene expression or Hr activity. A clone library of gene fragments inserted into a promoter probe vector can be constructed to operably link the gene fragment with a reporter gene, such that a promoter contained in the gene fragment may direct the transcription of the indicator gene. A suitable indicator gene will be transcribed and produce a detectable indicator product under appropriate assay conditions. Individual clones of the library may be introduced into the host cell, and colonies replica plated under conditions of hairless induction or noninduction. Gene fragments will be isolated from colonies which produce indicator product only when hairless activity is induced because they could contain Hr-dependent promoters. Alternatively, a construct containing the indicator gene but no operably linked promoter may be randomly integrated into the chromosome of a cell. Clones which contain integrations near Hr-dependent promoters may be identified after induction of hairless activity by screening for the indicator product. Those integration sites could mark the sites of Hr-dependent promoters and isolating the Hr-dependent genes associated with such promoters may also identify Hr-dependent genes.

Differentially expressed genes may be isolated and cloned through differential message display, RNA fingerprinting, representational difference analysis (RDA), subtractive hybridization, substraction between electronic databases, differential screening of arrayed cDNA clones or libraries, reciprocal subtraction differential display, serial analysis of gene expression, and generation of expressed sequence tags (ESTs). See Soares (Curr. Opin. Biotechnol., 8, 542–546, 1997) and references cited therein. Hairless-regulated genes whose expression is correlated temporally with at least one of the anagen/catagen/telogen stages of the cycle, or spatially in a balding region of the scalp are especially desired.

Transcriptional and/or translational fusions of Hairless and a heterologous polynucleotide or polypeptide, respectively, are considered to be encompassed by the invention. In a transcriptional fusion, a non-translated region of the heterologous gene may be ligated to the Hairless gene or, alternatively, a non-translated region of the Hairless gene may be ligated to the heterologous gene. The reading frames of Hairless polypeptide and a heterologous polypeptide may be joined in a translational fusion. If a reporter or selectable marker is used as the heterologous polynucleotide/polypeptide, then the effect of mutating the nucleotide/amino acid sequences of Hairless or heterologous polynucleotide/polypeptide on Hairless function may be readily assayed. In particular, a transcriptional fusion may be used to localize a regulated promoter of the Hairless gene and a translational fusion may be used to localize Hairless protein in the cell. For polypeptide fusions, a peptide recognition site for a protease (e.g., enterokinase, Factor Xa, thrombin) may also be included to separate peptide domains and to isolate them from each other.

For example, a chimera with domains from Hairless and a heterologous protein may be produced. The heterologous protein may be a transcription factor such as those described in Locker, *Transcription Factors: Essential Data*, Wiley, 1996. The domain may include a sequence motif such as a helix-turn-helix, a zinc finger, a leucine zipper, or combinations thereof. A function such as sequence-specific binding, activation or silencing of transcription, oligomerization, or combinations thereof may be associated with the domain. The domain may be derived from another mammalian transcription factor (e.g., nuclear hormone receptor with an identified ligand or orphan receptor), a prokaryotic transcription factor (e.g., LexA), or a lower eukaryotic transcription factor (e.g., GAL4)

According to another aspect of the invention, the Hairless DNA is transcribed to produce Hairless RNA transcript, the Hairless RNA is translated to produce Hairless nascent chain, the Hairless nascent chain folds to produce Hairless protein in its native conformation, and the native Hairless protein is processed to produce a modified Hairless protein with any native post-translation modifications (e.g., acylation, disulfide linkage, glycosylation, phosphorylation, proteolytic cleavage, sulfation). Nascent chain, native protein, and modified protein are known generically as polypeptide. In analogy to rodent sequences, human Hairless polypeptide may have a relative mobility of about 127 KDa in denaturing SDS-PAGE.

Hairless polypeptide and its variants (i.e., deletion, domain shuffling, insertion, substitution, and combinations thereof are useful for determining structure-function relationships (e.g., alanine scanning, conservative or non-conservative amino acid substitution). See Wells (Bio/Technology, 13, 647–651, 1995) and U.S. Pat. No. 5,534,617. Variant Hairless polypeptides are encoded by suitable variant Hairless polynucleotides.

Structure-function relationships of Hairless may be studied using variant polypeptides in a transcription assay. Thus, mutations in discrete domains of the Hairless polypeptide may be associated with hormone receptor binding, activation of transcription, repression of transcription, or combinations thereof. Binding studies may also be used to identify and isolate a natural ligand for Hairless. Chemical agents which bind Hairless may be useful for modulating (i.e., activating or repressing) its transcriptional activity.

A human Hairless polynucleotide, polypeptide, or specific binding molecule may be used to identify and detect this genetic marker in family pedigrees (e.g., CEPH/NIH or Utah projects), radiation hybrids, or human-rodent somatic cell hybrids. Fingerprinting would allow identification of an individual within a genetically similar population or construction of a genealogy among genetically related individuals. Genetic divergence during the evolution of mammals would predict that the human gene and protein would be more similar to other primates, than to primates. Thus, genetic differences as reflected in the affinity of specific binding molecules or sequence comparisons may be used in molecular taxonomy to determine evolutionary relatedness of different species.

Mutations that are functionally significant and polymorphisms in Hairless nucleotide and amino acid sequences are also an aspect of the invention. Such variants may be mutations or polymorphisms found as natural variations in the population without phenotypic consequence, or may be affect biological function by increasing or decreasing transcriptional activity. Comparison of SEQ ID NOS:2–4 shows several possible polymorphisms. Ahmad et al. (Science, 279, 720–724,1998) and Cichon et al. (Hum. Mol. Genet., 7,1671–1679 and 1987–1988, 1998) describe mutations that may cause congenital alopecia. Mutations may be located in regulatory and/or coding regions of the gene, they are useful to establish structure-function relationships in the disclosed amino acid sequence.

For example, a retroviral insertion which reduces the steady-state level of mouse Hairless message is responsible for the phenotype. The rhino allele exhibits no or little message in a $hr^{rh}/hr^{rh}$ homozygote. Such a null (or almost null) mutant, or a cell derived therefrom, may serve as a host for introduction of an expression construct. A dominant allele $Hr^{n}$ (near naked) has is also being characterized. See, generally Sundberg, *Handbook of Mouse Mutations with Skin and Hair Abnormalities*, CRC Press, 1994.

Genetic polymorphism in the Hairless gene may be used in linkage mapping, genetic fingerprinting, molecular taxonomy, and to study the role of Hairless in quantitative trait linkage (QTL), especially alopecia. For example, detection of a restriction fragment length polymorphism (RFLP), random amplified polymorphic DNA (RAPD), amplified fragment length polymorphism (AFLP), single-stranded conformational polymorphism (SSCP), single nucleotide polymorphism (SNP), short tandem repeat (STR), variable nucleotide tandem repeat (VNTR), or micro-satellite length heterogeneity may be linked to a genetic trait or phenotype. Such polymorphisms (or mutations if the polymorphism results in a mutant phenotype) may also be useful to investigate gene expression and development.

Detection of a germline or somatic mutation will determine that a disease is inherited or acquired, respectively. Identification of mutations by molecular genetic or cytogenetic techniques may also determine how Hairless expression is regulated during development.

The Hairless nucleotide sequence can be used to produce a fusion polypeptide with at least one heterologous peptide domain (e.g., an affinity or epitope tag). Polypeptide antigens are useful for producing specific antibody and epitope mapping of Hairless-specific antibody. Hairless polypeptide may be any length between about 5 amino acid residues to about 1250 amino acid residues. Preferably, it is produced in soluble form and/or refolded in native conformation. Polypeptide may be conjugated to either member of a specific binding pair (e.g., antibody-digoxygenin/hapten/peptide, biotin-avidin/streptavidin, GST-glutathione, MBP-maltose, polyhistidine-nickel, protein A/G-immunoglobulin).

Polypeptide may be synthesized by chemical means, purified from natural sources, synthesized in transfected host cells, or combinations thereof. Polypeptide synthesized in transfected bacteria from an expression construct will be non-glycosylated but, if eukaryotic post-translational modifications are desired, the expression construct may be transfected into a suitable eukaryotic cell (e.g., yeast, insect, hamster, mouse, rat, somatic, stem, non-human zygote) or organism (e.g., insect, non-human mammal, hamster, mouse, rat, plant). Hairless polynucleotide per se or an expression construct comprising the Hairless polynucleotide may be introduced into the host cell or organism by a process such as chemical transfection (e.g., calcium phosphate, cationic liposome, DEAE-dextran, polybrene), electroporation, genetic immunization, infection by recombinant virus, or microinjection. Preferably the introduced polynucleotide is an expression construct and the expression construct integrates into the eukaryotic genome of the host cell or organism. See, for example, Goeddel, *Gene Expression Technology*, Academic, 1990; Murray, *Gene Transfer and Expression Protocols*, Humana, 1991; Tuan, *Recombinant Gene Expression Protocols*, Humana, 1997; Tuan, *Recombinant Protein Protocols*, Humana, 1997.

According to another aspect of invention, a set of oligonucleotides may be selected from the Hairless nucleotide sequence. This set of primers will be specific for amplification of Hairless gene and can be used as a pair for PCR and RT-PCR amplification of DNA and RNA, respectively; a single oligonucleotide can be used for specific hybridization to a Hairless nucleotide sequence.

The polynucleotide may be ligated to a linker nucleotide sequence or conjugated to one affinity tag of a specific binding pair (e.g., antibody-peptide epitope/digoxygenin/hapten, biotin-avidin/streptavidin, GST-glutathione, MBP-maltose, polyhistidine-nickel, protein A/G-immunoglobulin). The polynucleotide may be conjugated to the affinity tag by ligation of a nucleotide sequence encoding the affinity tag or by direct chemical linkage to a reactive moiety on the affinity tag by crosslinking.

Polynucleotide and/or polypeptide of the invention may be used as an affinity tag to identify, isolate, and detect interacting proteins that bind the Hairless gene or protein. Such interacting proteins may regulate Hairless gene expression (e.g., affinity chromatography of sequence-specific DNA-binding proteins, electrophoretic mobility shift assay, footprinting, methylation interference, one-hybrid system) or form protein complexes with regulate the cellular function of Hairless (e.g., crosslinking of protein complexes, screening a phage display library, two-hybrid system). The invention is not limited to such protein agents but may also be used to identify, isolate, and detect other chemical agents which may regulate Hairless gene expression or Hairless protein function by screening, for example, a combinatorial or natural product library for agents which potentiate or inhibit the growth and maintenance of hair.

Further, the polynucleotide, polypeptide, and specific binding molecule may be optionally attached to a solid substrate (e.g., glass or silanized slide, magnetic bead, microtiter plate, nitrocellulose, nylon, resin bead). Such reagent would allow capture of a molecule in solution by a specific interaction between the cognate molecules and immobilization of the solution molecule on the solid substrate. See, for example, U.S. Pat. Nos. 5,143,854; 5,639,603; 5789,162; and 5,789,172. Monitoring Hairless expression is facilitated by using biochips or microarrays. See, for example, U.S. Pat. Nos. 5,445,934; 5,510,270; 5,545,531; 5,677,195; and a special supplement (Nat. Genet., 21,1–60, 1999).

Nucleotide and amino acid sequences may be synthesized in situ on the substrate by solid phase chemistry or photolithography. In situ synthesis attaches the nucleotides or amino acids directly to the substrate. Alternatively, the polynucleotide, polypeptide, or specific binding molecule may be attached by interaction of a specific binding pair (e.g., antibody-digoxygenin/hapten/peptide, biotin-avidin/streptavidin, GST-glutathione, MBP-maltose, polyhistidine-nickel, protein A/G-immunoglobulin); crosslinking may be used if covalent attachment to the substrate is desired. Glutaraldehyde is a covalent bifunctional crosslinker suitable for immobilization on a substrate, but a photoactivatable, reversible crosslinker is preferred to identify and isolate molecules interacting in a complex (e.g., a thiol linkage that may be reduced).

Hybridization may take place in solution or on a solid substrate. If either the Hairless polynucleotide or probe that undergoes hybridization is attached to a solid substrate (e.g., glass or silanized slide, magnetic bead, microtiter plate, nitrocellulose, nylon, resin bead), hybridization will result in capture of the unattached species.

An overlapping set of polypeptides which define all possible linear epitopes of Hairless may be arranged on a solid substrate to map the epitope specifically bound by a binding molecule (e.g., polyclonal or monoclonal antibody). See U.S. Pat. No. 5,194,392. Once a reactive epitope is defined, it may be used to isolate the specific binding molecule or to inhibit binding between Hairless and the specific binding molecule. A polypeptide or specific binding molecule thereof may be used to establish a profiling reference panel, and thereby isolate, detect, or otherwise characterize the chemical agents of the invention. See U.S. Pat. Nos. 5,384,263; 5,541,070; and 5,798,275.

Multiplex analysis may be used to monitor Hairless expression together with expression of another transcription factor (e.g., thyroid hormone and ROR orphan receptors) or combinations thereof. Such multiplex analysis may be performed using different polynucleotides or polypeptides arranged in high density on a solid substrate (i.e., a microarray). However, simultaneous solution methods such as multi-probe ribonuclease protection assay or multi-primer pair polynucleotide amplification associate each transcript with a different length of detected product which is resolved by separation according to molecular weight.

Related nucleotide sequences may be defined by a combination of structural and functional criteria. For example, related nucleotide sequences derived from the human Hairless sequence may hybridize under stringent conditions known in the art. Suitable conditions for oligonucleotides 50 bases or less could be 400 mM NaCl, 40 mM PIPES pH 6.4, 1 mM EDTA, 50° C. or 70° C. (see Beltz et al., Meth. Enzymol., 100, 266–285,1983); and suitable conditions for polynucleotides longer than 50 bases could be 500 mM $NaHPO_4$ pH 7.2, 7% mM sodium dodecyl sulfate (SDS), 1% bovine serum albumin (BSA), 1 mM EDTA, 65° C. (Church and Gilbert, Proc. Natl. Acad. Sci. USA, 81, 1991–1995, 1984). Short, conserved peptide domains may be used to design amplification primers which probe for related nucleotide sequences (Gould et al., Proc. Natl. Acad. Sci. USA, 86,1934–1938,1989).

However, these are all rather strict definition because some nucleotide sequences which encode the Hairless polypeptide with 100% identity (i.e., a functional equivalent of the native Hairless polynucleotide) would fail to hybridize under stringent conditions because of the redundancy of the genetic code, but are desirable for use in an expression construct because of the preferences of host cells and organisms for certain codons.

An "isolated" polynucleotide or polypeptide is at least partially isolated from the source of the polynucleotide or polypeptide. Using the nucleotide and amino acid sequences disclosed herein, compositions or extracts of the invention may be made substantially pure by controlled expression of the polynucleotide or polypeptide, and isolating same. Expression may be accomplished by extraction from natural sources, recombinant technology, or chemical synthesis.

By "substantially pure", a composition or extract containing a molecule is described as being at least 80%, preferably at least 90%, more preferably at least 95%, and most preferably at least 99% pure by weight as compared to other substances (i.e., contaminants) of the same chemical character as the recited molecule (e.g., nucleotide, amino acid).

Thus, a "purified" polynucleotide or polypeptide is assessed relative to the starting source (e.g., cytoplasm, nucleoplasm, cellular or nuclear lysate, cellular or tissue extract) from which purification was initiated.

Preferably, such compositions or extracts are reduced by at least 95% of the initial number of intact cells and/or viral particles (i.e., 95% free). A substantially cell-free composition or extract is reduced by at least 99% of the initial number of intact cells and/or viral particles, and a reduction of at least 99.99% may also be achieved. Compositions or extracts may also be cleared so that they are substantially free of membranes or membrane-bounded structures (reduced by at least 95% of the initial membrane content by weight).

Binding is described as "specific" for binding which is able to discriminate Hairless polynucleotide or polypeptide from a mixture of other chemical substances which are not related to Hairless. Processes of isolation, detection, and identification may depend on specific binding of Hairless polynucleotide or polypeptide in the mixture. The skilled artisan would be able to determine appropriate process conditions to achieve specific binding by choice of length of time, temperature, salt concentration, surfactant, pretreatment (e.g., adsorption, affinity purification, subtraction), and post-treatment (e.g., additional rounds of binding, signal amplification, washing).

The meaning of "heterologous" depends on context. For example, heterologous polynucleotide regions or polypeptide domains may mean that some regions/domains are not found in the same species in nature (e.g., a human polynucleotide encoding Hairless and a prokaryotic-derived promoter). Another example is that heterologous polynucleotide regions or polypeptide domains may mean that the regions/domains are not found joined together in nature (e.g., a human Hairless polypeptide and a MYC epitope tag, nuclear localization signal, or DNA binding domain). Ligation of polynucleotide regions or fusion of polypeptide domains occurs by inventive manipulation, such as by de novo synthesis or recombination. Of course, such joining may be preceded or followed by fragmentation (e.g., hydrolysis of a phosphodiester or peptide bond) through enzymatic (e.g., nuclease or protease) or chemical methods. In a further example, transfection of an expression construct into a heterologous host cell or heterologous non-human transgenic animal means that the expression construct is not found in the cell's or animal's genome in nature.

Similarly, the meaning of "native" depends on context. For a human polynucleotide or polypeptide, it may mean that the polynucleotide/polypeptide was purified from a human source, has a sequence identical to a non-mutant human Hairless gene or protein, shares a conformation with properly folded polynucleotide/polypeptide, or is not denatured.

Standard techniques in the art are described in Ausubel et al., *Current Protocols in Molecular Biology*, Wiley, 1998; Birren et al., *Genome Analysis Series*, CSHL, 1997–1999; Coligan et al., *Current Protocols in Immunology*, Wiley, 1998; Coligan et al., *Current Protocols in Protein Science*, Wiley, 1998; Diffenbach and Dveksler, *PCR Primer*, CSHL, 1995; Dracopoli et al., *Current Protocols in Human Genetics*, Wiley, 1998; Harlow and Lane, *Antibodies and Using Antibodies*, CSHL, 1988 and 1999; Hogan et al., *Manipulating the Mouse Embryo*, CSHL, 1994; Janson and Ryder, *Protein Purification*, Wiley, 1997; Marshak et al., *Strategies for Protein Purification and Characterization*, CSHL, 1996; Mullis et al., *The Polymerase Chain Reaction*, Birkhauser, 1994; Murphy and Carter, *Trangenesis Techniques*, Humana, 1993; Pinkert, *Trangenic Animal Technology*, Academic, 1994; Sambrook et al., *Molecular Cloning*, CSHL, 1989; Spector et al., *Cells*, CSHL, 1998.

All publications, applications, and patents cited in this specification are indicative of the skill in the art, and are incorporated herein by reference in their entirety.

The following examples are meant to be illustrative of the present invention, however the practice of the invention is not limited or restricted in any way by them.

EXAMPLES

Thyroid hormone is a critical mediator of central nervous system (CNS) development, acting through nuclear receptors to modulate the expression of specific genes. Transcription of the rat hairless (hr) gene is highly up-regulated by thyroid hormone in the developing CNS; it is shown here that hr is directly induced by thyroid hormone. By identifying proteins that interact with the hr gene product (hr), it was found that hr interacts directly and specifically with thyroid hormone receptor (TR)—the same protein that regulates its expression. hr associates with TR and not with retinoid or steroid receptors; this specificity distinguishes hr as the only interacting protein known to date that binds to a single nuclear receptor. hr can act as a transcriptional repressor, suggesting that its interaction with TR is part of a novel autoregulatory mechanism. Many factors, both genetic and environmental, contribute to the formation and function of the mammalian central nervous system (CNS). An essential component of these processes is thyroid hormone; if thyroid hormone levels are perturbed, abnormal development ensues resulting in neurological deficits that include severe mental retardation. The effects of thyroid hormone (TH) are mediated through the action of specific nuclear receptor proteins. Thyroid hormone receptors (TR) act by binding to specific DNA sequences and subsequently activating or repressing the transcription of nearby genes in response to hormone binding. Several proteins that interact with TR and other nuclear hormone receptors, including both co-activators and co-repressors, have been identified (Horwitz et al., Mol. Endocrinol., 10, 1167–1177, 1996; Beato and Sánchez-Pacheco, Endocrine Reviews, 17, 587–609, 1996).

Although much is known about the mechanism of action of thyroid hormone and other nuclear receptors, far less is known about the genes regulated by these receptors. The rat hairless (hr) gene has been shown to be up-regulated (>10-fold) by thyroid hormone in developing brain (Thompson, J. Neurosci., 16, 7832–7840, 1996). The rapid induction (<4 hours) occurs even in the absence of protein synthesis, suggesting that hr is directly regulated by TR. Direct target genes are particularly important because such genes likely constitute the first step in the genetic program responsible for TH-mediated aspects of neural development. It is shown here that the upstream regulatory region of the hr gene includes a potent thyroid hormone response element (TRE), indicating that hr is indeed a direct target of TR.

The murine hr locus was originally identified as a spontaneous mutation caused by an endogenous retrovirus (Stoye et al., Cell, 54, 383–391, 1988). The hr gene is expressed predominantly in skin and brain; the mutant phenotype in skin is progressive hair loss and increased susceptibility to cancer, the neurological phenotype has not yet been described (Thompson, J. Neurosci., 16, 7832–7840, 1996; Cachon-Gonzalez et al., Proc. Natl. Acad. Sci. USA, 91, 7717–7721, 1994). The hr gene encodes a putative protein of approximately 130 KD that lacks homology to known structural motifs other than a cluster of cysteine residues proposed to form a zinc finger (Cachon-Gonzalez et al., Proc. Natl. Acad. Sci. USA, 91, 7717–7721, 1994).

Towards defining the function of the hr gene product (hr), proteins that interact with hr were identified. Surprisingly, it was found that hr interacts with TR. Previously identified proteins that interact with TR have been shown to interact with multiple nuclear receptors (Baniahmad et al., Proc. Natl. Acad. Sci. USA 90, 8832–8836, 1993; Oñate et al., Science, 270, 1354–1357, 1995; Lee et al., Nature, 374, 91–94, 1995; Chen and Evans, Nature, 377, 454–457, 1995; Hörlein et al., Nature, 377, 397–404,1995; Zeiner and Gehring, Proc. Natl. Acad. Sci. USA, 92, 11465–11469, 1995; Horwitz et al., Mol. Endocrinol., 10, 1167–1177, 1996; Beato and Sánchez-Pacheco, Endocrine Reviews, 17, 587–609, 1996; L'Horset et al., Mol. Cell Biol., 16, 6029–6036,1996; vom Baur et al., EMBO J., 15, 110–124, 1996). In contrast, hr interacts only with TR. The interaction of hr with TR suggests that hr is part of a novel autoregulatory mechanism by which hr may influence the expression of downstream TH-responsive genes.

hr Gene Expression is Directly Regulated by Thyroid Hormone

A rat genomic library (Stratagene) was screened using a 450 bp probe from the 5' end of the hr cDNA. Four overlapping clones were isolated. A 15 Kb Not I fragment was digested with Ksp I and the resulting 6 and 9 Kb fragments subcloned into pBluescript (Stratagene). The subcloned fragments were digested with Alu I and used for gel shift analysis. Proteins were synthesized by coupled in vitro transcription/translation (Promega) in the presence of $^{35}$S-methionine (NEN). Synthesis was analyzed by running a fraction of the radiolabeled products on a gel followed by autoradiography. DNA binding reactions contained approximately 200 ng of digested DNA mixed with $^{35}$S-TR and RXR. Samples were run on 5% polyacrylamide gels in 0.5×TBE, fixed, dried and exposed to X-ray film. Fragments that gave shifted bands were restriction mapped and smaller fragments subcloned. The subcloned fragments were digested with Alu I and used for DNA binding. This process was repeated until the smallest binding fragment was determined to be a 106 bp Hinf I-Eag I fragment. After sequencing the 106 bp fragment (SEQ ID NO:7 includes the named restriction sites), overlapping oligonucleotides spanning the fragment were synthesized and used as competitors for DNA binding. The functionally equivalent mouse nucleotide sequence is SEQ ID NO:8. For transfection experiments, oligonucleotides were cloned upstream of a minimal thymidine kinase promoter by digesting tk-luc with Hind III, then ligating the annealed, phosphorylated oligonucleotides. Constructs were sequenced to determine number of oligonucleotides present and to confirm the sequence and orientation.

To determine if hr is a direct target of thyroid hormone receptor (TR), cis-acting sequences were examined to determine whether controlling its expression include a binding site for TR and/or TR/retinoid X receptor (RXR) heterodimers. Genomic sequences from the hr gene were digested with frequent cutting restriction enzymes and used as probes in a gel retardation assay using $^{35}$S-TR. No binding was observed when fragments were incubated with $^{35}$S-TR alone, but binding was detected when both TR and RXR (unlabeled) were present. A high affinity TR/RXR binding site was detected within a 9 Kb Not l-Ksp I fragment immediately upstream of the hr transcription unit. By subcloning and testing progressively smaller restriction fragments, the TR/RXR binding site was mapped to within 106 bp located approximately 9 Kb upstream of the first exon. The isolated, $^{32}$P-labeled 106 bp sequence bound specifically to TR/RXR heterodimers, as binding was competed by TRE-containing oligonucleotides (DR4, synthetic direct repeat TRE; MLV, Moloney Leukemia virus TRE) but not by a mutated TRE (MHC-M, mutated TRE from β-myosin heavy chain gene) or a retinoic acid response element (RARE, retinoic acid response element DR5) (Umesono et al., Cell, 65, 1255–1266, 1991).

To more precisely define the TR/RXR binding site, overlapping oligonucleotides encompassing the 106 bp sequence were synthesized and used as competitors for binding to the 106 bp fragment. Only oligonucleotides C and E were effective competitors, and they both contained the TR/RXR binding site. These oligonucleotides share a 23 bp sequence that includes an imperfect direct repeat (ggtggAGG <u>G</u>CATCTGAGG<u>A</u>CAtc, SEQ ID NO:9) separated by four nucleotides. TREs often consist of half sites spaced by four nucleotides (DR+4), with an optimal half site of AGGTCA. Both half sites of the hr TRE match the optimal half site in five of six positions. Thus, the hr gene has a potential TRE of the consensus type DR+4. The minimal sequence assayed that conferred thyroid hormone responsiveness and binds TR/RXR is SEQ ID NO:10. The mouse sequence is identical.

GH1 (rat pituitary) cells were obtained from ATCC and maintained in DMEM supplemented with 10% fetal calf serum. For induction experiments, serum was depleted of thyroid and steroid hormones by treatment with AG-1-X8 resin (Bio-Rad) and charcoal (Sigma) as described (Samuels et al., Endocrinology, 105, 80–85, 1979). Cells were grown for one day in hormone depleted media before transfection. Transfection was by lipofection (LIPOFECTAMINE, Gibco-BRL) in 6-well plates. After transfection, thyroid hormone (L-$T_3$) was added to $10^{-7}$ M. Cells were transfected (per well of a 6-well plate) with 167 ng of reporter plasmid, 50 ng of expression plasmid and 80 ng of CMX-βgal. Cells were harvested using 1× reporter lysis buffer (Promega) and assayed for β-galactosidase and luciferase activity.

To test whether the direct repeat sequence motif indeed confers thyroid hormone responsiveness, the 106 bp fragment and putative TRE oligonucleotides were individually placed upstream of a minimal thymidine kinase (tk) promoter driving expression of a luciferase reporter gene. Introduction of these constructs into GH1 cells, which express endogenous thyroid hormone receptors, showed that transcription is activated in the presence of thyroid hormone, only when the direct repeat sequence is present (106HE-tkluc, C-tkluc). Therefore, the direct repeat sequence in the hr gene acts as a TRE. Together with previous data showing that up-regulation of hr by thyroid hormone occurs rapidly (<4 hours) and without the need for new protein synthesis (Thompson, J. Neurosci., 16, 7832–7840, 1996), these results demonstrate that hr is a direct response gene for thyroid hormone, the first such gene identified in the mammalian CNS.

hr Interacts with TR

To construct pLexA-hr, a 2.2 Kb Hind III fragment corresponding to amino acids 575–1215 of hr (FIG. 1) was isolated, the ends filled-in with Klenow large fragment, Bam HI linkers ligated, and then cloned into the Bam HI site of pLexA (Hollenberg et al., Mol. Cell Biol., 15, 3813–3822, 1995). The resulting plasmid was transformed into yeast strain L40 (Hollenberg et al., ibid.). The resulting strain was used to screen a human brain cDNA library constructed as a fusion with the activation domain of VP16. DNA was isolated from HIS+, lacZ+ colonies (Robzyk and Kassir, Nucleic Acids Res., 20, 3790, 1992), propagated in *E. coli*, purified and sequenced. Cells were tested for β-galactosidase activity as described (Reynolds and Lundblad, in *Short Protocols in Molecular Biology*, Ausubel et al., eds., John Wiley, New York, p.13–27, 1992). To test the hormone dependence of interaction, TRIAC (Sigma) was added to the media and assay buffer (final concentration $10^{-6}$ M).

To begin to understand the function of the hr gene product (hr), proteins were identified that interact with hr by using a two-hybrid assay (Hollenberg et al., ibid.). The C terminal 639 amino acids of hr (amino acids 575–1215 as shown in FIG. 1, includes the putative zinc finger) were fused to the lexA DNA binding domain and used as "bait" (LexA-hr) to screen a human brain cDNA library. One cDNA that was isolated multiple times (2H11) was characterized. Remarkably, clone 2H11 encodes a thyroid hormone receptor (TRα2, amino acids 14–490) (Lazar, Endocrine Rev., 14,184–193, 1993). However, interaction is not limited to the TRα2 isoform, as TRα1 was found to interact as well. TRα1 is a functional TR, while TRα2, which has a divergent C terminus, lacks the ability to bind thyroid hormone; the preference for isolating TRα2 is likely because the mRNA for TRα2 is more abundant than that for TRα1. Interaction was moderately influenced by hormone, as interaction of TRα1 was reduced two-fold by hormone binding. Thus, it appears that the product of the hr gene, a direct target of transcriptional regulation by TR, interacts with the same factor that regulates its expression.

Far Western Assay

TrpE-hr was constructed by insertion of a 2.2 Kb Hind III fragment corresponding to amino acids 575–1215 of hr into pATH21 (kindly provided by N. Patel). GST-hr was constructed by insertion of the 2.2 Kb Bam HI fragment from pLexA-hr into pGEX3X (kindly provided by J. Shuman). GST-RXR and GST-TR were obtained from Santa Cruz Biotechnology. Extracts from bacteria expressing fusion proteins were separated by SDS-polyacrylamide gel electrophoresis and transferred to nitrocellulose. After transfer, filters were prepared for far western blotting as described (Cavaillès et al., Proc. Natl. Acad. Sci. USA, 91, 10009–10013, 1994) except that $^{35}$S-labeled proteins were used as probes. pTZ18 (rTRβ1) was kindly provided by H. Towle; pCMX TRα1, pCMX hRARα and pCMX hRXRα were kindly provided by K. Umesono.

To confirm the direct interaction between hr and TR, a far western assay was used. hr (amino acids 575–1215) was expressed in bacteria as a fusion protein with either glutathione S transferase (GST) or TrpE. Extracts from bacteria expressing hr fusion proteins were separated by SDS-polyacrylamide gel electrophoresis and transferred to nitrocellulose: TrpE-Srg1 (negative control), TrpE-hr, GST only, and GST-hr. The immobilized, renatured proteins were incubated with $^{35}$S-TRα1. TRα1 detected a protein the size of the hr fusion proteins, which was recognized by hr-specific antisera. Therefore, hr interacts specifically with TRα1. These data also show that no other factors (for example, other proteins in yeast) are required for this interaction.

Previously identified factors that interact with TR have been shown to also associate with retinoid receptors, and in some cases, other nuclear receptors as well. To examine the specificity of interaction between TR and hr, hr was tested for interaction with TRβ1, retinoic acid receptor (RAR) and retinoid X receptor (RXR). TRβ1 bound as well as TRα1 to the hr fusion protein, indicating that interaction is not isoform-specific. In contrast, binding was not detected with RAR or RXR. $^{35}$S-RAR interacted with RXR, and $^{35}$S-RXR interacted with TR, verifying that RAR and RXR are functional in this assay. Consistent with these results, RAR did not interact with hr in the two-hybrid assay. Two steroid hormone receptors (glucocorticoid and mineralocorticoid) were tested for interaction using the far western assay, and also failed to interact with hr. Therefore, of the receptors tested, binding is specific for TR. These results are particularly important because they distinguish hr as the only protein known to date that binds specifically to a single nuclear receptor.

Immunohistochemistry and in Vivo Transcription Activity

GH1 and CHO cells were obtained from ATCC and maintained in DMEM supplemented with 10% fetal calf serum. Transfection was by lipofection (LIPOFECTAMINE, Gibco-BRL) in 6-well plates. Cells were transfected (per well of a 6-well plate) with 167 ng of reporter plasmid, 50 ng of expression plasmid and 80 ng of CMX-βgal. pCMX-GAL-hr was constructed by inserting the Bam HI fragment from pLexA-hr into pCMX-GAL4. pCMX-GAL4, GALpx3 tkluc, pCMX GAL-RXR were kindly provided by K. Umesono. Cells were harvested using 1× reporter lysis buffer (Promega) and assayed for β-galactosidase and luciferase activity.

In addition to their interaction in vitro, hr and TR are expressed in the same cell types in vivo. It was shown previously that hr is expressed in tissues that express TR; in situ hybridization analyses have shown that hr and TR transcripts are present in the same cell populations in the brain (Murray et al., J. Biol. Chem., 263, 12770–12777, 1988; Bradley et al., J. Neurosci., 12, 2288–2302, 1992; Thompson, J. Neurosci., 16, 7832–7840, 1996). For interaction of hr and TR to occur in vivo, both must occupy the same subcellular compartment. TR resides in the nucleus; to determine if hr is also nuclear, sequences encoding an epitope (MYC) detected by a specific monoclonal antibody were appended to the hr cDNA (MYC-hr).

An epitope for MYC was appended to the amino terminus of hr at amino acid 200 by subcloning a 3.1 Kb Bam HI-Xba I fragment of hr into the vector pBS KS+MYC (kindly provided by M. Bellini). The resulting MYC-hr fusion was excised by digestion with Xba I and partial digestion with Hind III to isolate a 3.2 Kb fragment, which was inserted downstream of the RSV LTR. The resulting cDNA was transfected into GH1 cells, and the MYC epitope detected by immunofluorescence. GH1 cells were grown on coverslips and transfected by lipofection. Cells were fixed with 1.6% paraformaldehyde for 20 minutes at room temperature, blocked for 30 minutes in PBS with 5% normal goat serum and incubated with a mouse monoclonal antibody to MYC (9E10, kindly provided by Z. Wu) for 1 hour. Detection was with cyanine dye CY3 anti-mouse antibody (Jackson ImmunoResearch). Cells were mounted in 50% glycerol with 0.25 μg/ml DAPI to counterstain nuclei. Nuclear staining was observed in cells transfected with MYC-hr but not in control cells. Identical results were obtained using hr-specific antisera. Thus, like TR, hr is a nuclear protein.

Identical results were obtained using the hr-specific antisera raised to the GST-hr fusion protein described above. Antiserum specific to the carboxyl terminal region of Hr were generated by injecting individual rabbits with acrylamide containing either the trpE-Hr fusion protein (Hr amino acids 575–1215) or a GST-Hr fusion protein (Hr amino acids 730–1215) using a standard injection schedule. Serum from rabbits injected with either fusion protein recognizes a protein band with the predicted size of Hr (i.e., about 127 KDa) on western blots using extracts from cells transfected with an expression construct containing the hr gene and not in extracts from control non-transfected cells. Cells transfected in parallel with RSV-βgal were used as a negative control for the anti-MYC antibody and stained with X-Gal as a positive control for transfection. The pattern of bands detected by the antiserum is more complicated in total protein extracts from tissue sources. The antiserum detects a band close to the predicted size of Hr but also several smaller bands. The multiple species detected may represent degradation products of Hr, alternative spliced/processed forms of Hr, related proteins that have a cross-reacting epitope, or combinations thereof. Further characterization of the specificity and sensitivity of this antiserum is in progress.

Since hr is a nuclear protein that interacts with a known transcription factor, hr was tested for a role in transcriptional regulation. When co-expressed with TR and a TRE-containing reporter, thyroid hormone induced transcription is reduced two fold, suggesting that hr acts as a repressor. To assay for endogenous repressor function, hr (amino acids 575–1215) was fused to the GAL4 DNA binding domain (DBD). hr/GAL4 plasmids were co-transfected with a GAL4 regulated promoter into CHO cells; all transfections included CMX-βgal as an internal control. When tested for the ability to repress transcription from a GAL4-dependent reporter, the GAL4 DBD-hr fusion protein reduced basal level transcription by about five fold. This effect is specific to hr sequences because the GAL4 DBD alone or a GAL4 DBD-RXR fusion protein did not affect activity. hr alone did not affect activity, indicating that repression by hr required tethering to DNA. The ability of hr to repress transcription indicates that when bound to thyroid hormone receptors, hr may function as a transcriptional modulator.

Discussion

Together with previous evidence that the hr gene is rapidly up-regulated by thyroid hormone even in the absence of protein synthesis, the mapping of a high affinity TRE in the hr gene demonstrates that hr is a direct target of thyroid hormone receptors in the developing mammalian CNS. Although a handful of genes whose expression is influenced by thyroid hormone in the CNS have been identified, induction of these genes has not been shown to be rapid (>24 hours) nor resistant to inhibitors of protein synthesis. Thus, hr is the first direct response gene for thyroid hormone identified in the developing mammalian nervous system. Given that postnatal CNS development is extremely sensitive to thyroid hormone (if thyroid hormone levels are perturbed, abnormal development ensues, resulting in neurological deficits that include severe mental retardation), expression of hr likely constitutes a key step in the genetic program responsible for TH-dependent aspects of CNS development.

The screen for proteins that interact with hr led to the startling discovery that the product of this thyroid hormone-responsive gene interacts directly and specifically with TR—the same protein that induces its expression. Equally important is the finding that although hr binds to TR, it does not bind to RAR or to their common partner, RXR. Though many proteins that interact with nuclear hormone receptors have been identified, all have been shown to be widely expressed and to bind to multiple receptors. In contrast, hr is predominantly expressed in brain and skin, and hr binds a single nuclear receptor, TR. hr and TR are both nuclear proteins, and are co-expressed in various regions of the brain, suggesting that the interaction observed in vitro also occurs in vivo.

The induction of hr expression by thyroid hormone, coupled with the interaction of hr protein with TR, suggests a novel autoregulatory pathway. Once induced by thyroid hormone, hr likely binds to TR, and through its repression function, modulates expression of downstream genes. The existence of a similar autoregulatory mechanism for other nuclear receptors is hinted at by the product of an estrogen-responsive gene (efp) that shows homology to the TIF/PML class of receptor interacting proteins (Inoue et al., Proc. Natl. Acad. Sci. USA, 90, 11117–11121, 1993; LeDouarin et al., EMBO J., 14, 2020–2033, 1995). As a direct target gene, together with its ability to interact with TR, hr likely serves a dual role—as a downstream target as well as upstream regulator of thyroid hormone action.

Human Hairless Gene and Protein Sequences

The human homolog of the rat hairless gene was cloned by screening a human motor cortex cDNA library (obtained from J. Arriza) using a rat hr cDNA as a probe (Hind III fragment, nucleotides 2088–4299; see accession number U71293 from Thompson, J. Neurosci., 16, 7832–7840, 1996). The library was screened with hybridization conditions of 50% formamide, 5×SSPE, 1× Denhardt's solution, 0.1% SDS, and 100 mg/ml denatured salmon sperm DNA at 42° C. for 16 hours. Four positive clones were detected (37MC1, 37MC3, 37MC6, 37MC12) and the cDNA inserts were obtained in plasmid form. The inserts of 37MC1, 6 and 12 were about 3.5 Kb and the insert of 37MC3 was about 2 Kb.

The nucleotide sequences from the 5' and 3' ends were determined for these cDNA inserts and found to be homologous to rat and mouse hr cDNAs. The full sequence of 37MC12 was determined by sequencing of both strands. The sequence of the longest cDNA clone corresponds to amino acid positions 232–1215 of the full-length human Hr as shown in FIG. 1.

In Table I, the human HR nucleotide sequence (SEQ ID NO:1) is aligned above its predicted amino acid sequence (SEQ ID NO:2).

TABLE I

TTT TAC TAC AAG GAT CCG AGC ATT CCC AGG TTG GCA AAG GAG CCC 45
Phe Tyr Tyr Lys Asp Pro Ser Ile Pro Arg Leu Ala Lys Glu Pro
1 5 10 15

TTG GCA GCT GCG GAA CCT GGG TTG TTT GGC TTA AAC TCT GGT GGG 90
Leu Ala Ala Ala Glu Pro Gly Leu Phe Gly Leu Asn Ser Gly Gly
20 25 30

CAC CTG CAG AGA GCC GGG GAG GCC GAA CGC CCT TCA CTG CAC CAG 135
His Leu Gln Arg Ala Gly Glu Ala Glu Arg Pro Ser Leu His Gln
35 40 45

AGG GAT GGA GAG ATC GGA GCT GGC CGG CAG CAG AAT CCT TGC CCG 180
Arg Asp Gly Glu Met Gly Ala Gly Arg Gln Gln Asn Pro Cys Pro
50 55 60

CTC TTC CTG GGG CAG CCA GAC ACT GTG CCC TGG ACC TCC TGG CCC 225
Leu Phe Leu Gly Gln Pro Asp Thr Val Pro Trp Thr Ser Trp Pro
65 70 75

GCT TGT CCC CCA GGC CTT GTT CAT ACT CTT GGC AAC GTC TGG GCT 270
Ala Cys Pro Pro Gly Leu Val His Thr Leu Gly Asn Val Trp Ala
80 85 90

GGG CCA GGC GAT GGG AAC CTT GGG TAC CAG CTG GGG CCA CCA GCA 315
Gly Pro Gly Asp Gly Asn Leu Gly Tyr Gln Leu Gly Pro Pro Ala
95 100 105

ACA CCA AGG TGC CCC TCT CCT GAG CCG CCT GTC ACC CAG CGG GGC 360
Thr Pro Arg Cys Pro Ser Pro Glu Pro Pro Val Thr Gln Arg Gly
110 115 120

TGC TGT TCA TCC TAC CCA CCC ACT AAA GGT GGG GAT CTT GGC CCT 405
Cys Cys Ser Ser Tyr Pro Pro Thr Lys Gly Gly Asp Leu Gly Pro
125 130 135

TGT GGG AAG TGC CAG GAG GGC CTG GAG GGG GGT GCC AGT GGA GCC 450
Cys Gly Lys Cys Glu Glu Gly Leu Glu Gly Gly Ala Ser Gly Ala
140 145 150

AGC GAA CCC AGC GAG GAA GTG AAC AAG GCC TCT GGC CCC AGG GCC 495
Ser Glu Pro Ser Glu Glu Val Asn Lys Ala Ser Gly Pro Arg Ala
155 160 165

TGT CCC CCC AGC CAC CAC ACC AAG CTG AAG AAG ACA TGG CTC ACA 540
Cys Pro Pro Ser His His Thr Lys Leu Lys Lys Thr Trp Leu Thr
170 175 180

CGG CAC TCG GAG CAG TTT GAA TGT CCA CGC GGC TGC CCT GAG GTC 585
Arg His Ser Glu Gln Phe Glu Cys Pro Arg Gly Cys Pro Glu Val
185 190 195

GAG GAG AGG CCG GTT GCT CGG CTC CGG GCC CTC AAA AGG GCA GGC 630
Glu Glu Arg Pro Val Ala Arg Leu Arg Ala Leu Lys Arg Ala Gly
200 205 210

AGC CCC GAG GTC CAG GGA GCA ATG GGC AGT CCA GCC CCC AAG CGG 675
Ser Pro Glu Val Gln Gly Ala Met Gly Ser Pro Ala Pro Lys Arg
215 220 225

CCA CCG GAC CCT TTC CCA GGC ACT GCA GAA CAG GGG GCT GGG GGT 720
Pro Pro Asp Pro Phe Pro Gly Thr Ala Glu Gln Gly Ala Gly Gly
230 235 240

TGG CAG GAG GTT CGG GAC ACA TCG ATA GGG AAC AAG GAT GTG GAC 765
Trp Gln Glu Val Arg Asp Thr Ser Ile Gly Asn Lys Asp Val Asp
245 250 255

TCG GGA CAG CAT GAT GAG CAG AAA GGA CCC CAA GAT GGC CAG GCC 810
Ser Gly Gln His Asp Glu Gln Lys Gly Pro Gln Asp Gly Gln Ala
260 265 270

TABLE I-continued

```
AGT CTC CAG GAC CCG GGA CTT CAG GAC ATA CCA TGC CTG GCT CTC   855
Ser Leu Gln Asp Pro Gly Leu Gln Asp Ile Pro Cys Leu Ala Leu
                275                 280                 285

CCT GCA AAA CTG GCT CAA TGC CAA AGT TGT GCC CAG GCA GCT GGA   900
Pro Ala Lys Leu Ala Gln Cys Gln Ser Cys Ala Gln Ala Ala Gly
                290                 295                 300

GAG GGA GGA GGG CAC GCC TGC CAC TCT CAG CAA GTG CGG AGA TCG   945
Glu Gly Gly Gly His Ala Cys His Ser Gln Gln Val Arg Arg Ser
                305                 310                 315

CCT CTG GGA GGG GAG CTG CAG CAG GAG GAA GAC ACA GCC ACC AAC   990
Pro Leu Gly Gly Glu Leu Gln Gln Glu Glu Asp Thr Ala Thr Asn
                320                 325                 330

TCC AGC TCT GAG GAA GGC CCA GGG TCC GGC CCT GAC AGC CGG CTC  1035
Ser Ser Ser Glu Glu Gly Pro Gly Ser Gly Pro Asp Ser Arg Leu
                335                 340                 345

AGC ACA GGC CTC GCC AAG CAC CTG CTC AGT GGT TTG GGG GAC CGA  1080
Ser Thr Gly Leu Ala Lys His Leu Leu Ser Gly Leu Gly Asp Arg
                350                 355                 360

CTG TGC CGC CTG CTG CGG AGG GAG CGG GAG GCC CTG GCT TGG GCC  1125
Leu Cys Arg Leu Leu Arg Arg Glu Arg Glu Ala Leu Ala Trp Ala
                365                 370                 375

CAG CGG GAA GGC CAA GGG CCA GCC CTG ACA GGG GAC AGC CCA GGC  1170
Gln Arg Glu Gly Gln Gly Pro Ala Val Thr Gly Asp Ser Pro Gly
                380                 385                 390

ATT CCA CGC TGC TGC AGC CGT TGC CAC CAT GGA CTC TTC AAC ACC  1215
Ile Pro Arg Cys Cys Ser Arg Cys His His Gly Leu Phe Asn Thr
                395                 400                 405

CAC TGG CGA TGT CCC CGC TGC AGC CAC CGG CTG TGT GTC GCC TGT  1260
His Trp Arg Cys Pro Arg Cys Ser His Arg Leu Cys Val Ala Cys
                410                 415                 420

GGT CGT GTG GCA GGC ACT GGG CGG GCC AGG GAG AAA GCA GGC TTT  1305
Gly Arg Val Ala Gly Thr Gly Arg Ala Arg Glu Lys Ala Gly Phe
                425                 430                 435

CAG GAG CAG TCC GCG GAG GAG TGC ACG CAG GAG GCC GGG CAC GCT  1350
Gln Glu Gln Ser Ala Glu Glu Cys Thr Gln Gln Ala Gly His Ala
                440                 445                 450

GCC TGT TCC CTG ATG CTG ACC CAG TTT GTC TCC AGC CAG GCT TTG  1395
Ala Cys Her Leu Met Leu Thr Gln Phe Val Ser Ser Gln Ala Leu
                455                 460                 465

GCA GAG CTG AGC ACT GCA ATG CAC CAG GTC TGG GTC AAG TTT GAT  1440
Ala Glu Leu Ser Thr Ala Met His Gln Val Trp Val Lys Phe Asp
                470                 475                 480

ATC CGG GGG CAC TGC CCC TGC CAA GCT GAT GCC CGG GTA TGG GCC  1485
Ile Arg Gly His Cys Pro Cys Gln Ala Asp Ala Arg Val Trp Ala
                485                 490                 495

CCC GGG GAT GCA GGC CAG CAG AAG GAA TCA ACA CAG AAA ACG CCC  1530
Pro Gly Asp Ala Gly Gln Gln Lys Glu Ser Thr Gln Lys Thr Pro
                500                 505                 510

CCA ACT CCA CAA CCT TCC TGC AAT GGC GAC ACC CAC AGG ACC AAG  1575
Pro Thr Pro Gln Pro Ser Cys Asn Gly Asp Thr His Arg Thr Lys
                515                 520                 525

AGC ATC AAA GAG GAG ACC CCC GAT TCC GCT GAG ACC CCA GCA GAG  1620
Ser Ile Lys Glu Glu Thr Pro Asp Ser Ala Glu Thr Pro Ala Glu
                530                 535                 540

GAC CGT GCT GGC CGA GGG CCC CTG CCT TGT CCT TCT CTC TGC GAA  1665
Asp Arg Ala Gly Arg Gly Pro Leu Pro Cys Pro Ser Leu Cys Glu
                545                 550                 555

CTG CTG GCT TCT ACC GCG GTC AAA CTC TGC TTG GGC CAT GAG CGA  1710
Leu Leu Ala Ser Thr Ala Val Lys Leu Cys Leu Gly His Glu Arg
                560                 565                 570
```

TABLE I-continued

```
ATA CAC ATG GCC TTC GCC CCC GTC ACT CCG GCC CTG CCC AGT GAT  1755
Ile His Met Ala Phe Ala Pro Val Thr Pro Ala Leu Pro Ser Asp
            575                 580                 585

GAC CGC ATC ACC AAC ATC CTG GAC AGC ATT ATC GCA CAG GTG GTG  1800
Asp Arg Ile Thr Asn Ile Leu Asp Ser Ile Ile Ala Gln Val Val
            590                 595                 600

GAA CGG AAG ATC CAG GAG AAA GCC CTG GGG CCG GGG CTT CG AGCT  1845
Glu Arg Lys Ile Gln Gln Lys Ala Leu Gly Pro Gly Leu Arg Ala
            605                 610                 615

GGC CCG GGT CTG CGC AAG GGC CTG GGC CTG CCC CTC TCT CCA GTG  1890
Gly Pro Gly Leu Arg Lys Gly Leu Gly Leu Pro Leu Ser Pro Val
            620                 625                 630

CGG CCC CGG CTG CCT CCC CCA GGG GCT TTG CTG TGG CTG CAG GAG  1935
Arg Pro Arg Leu Pro Pro Pro Gly Ala Leu Leu Trp Leu Gln Gln
            635                 640                 645

CCC CAG CCT TGC CCT CGG CGT GGC TTC CAC CTC TTC CAG GAG CAC  1980
Pro Gln Pro Cys Pro Arg Arg Gly Phe His Leu Phe Gln Gln His
            650                 655                 660

TGG AGG CAG GGC CAG CCT GTG TTG GTG TCA GGG ATC CAA AGG ACA  2025
Trp Arg Gln Gly Gln Pro Val Leu Val Ser Gly Ile Gln Arg Thr
            665                 670                 675

TTG CAG GGC AAC CTG TGG GGG ACA GAA GCT CTT GGG GCA CTT GGA  2070
Leu Gln Gly Asn Leu Trp Gly Thr Glu Ala Leu Gly Ala Leu Gly
            630                 685                 690

GGC CAG GTG CAG GCG CTG AGC CCC CTC GGA CCT CCC CAG CCC AGC  2115
Gly Gln Val Gln Ala Leu Ser Pro Leu Gly Pro Pro Gln Pro Ser
            695                 700                 705

AGC CTG GGC AGC ACA ACA TTC TGG GAG GGC TTC TCC TGG CCT GAG  2160
Ser Leu Gly Ser Thr Thr Phe Trp Glu Gly Phe Ser Trp Pro Glu
            710                 715                 720

CTT CGC CCA AAG TCA GAC GAG GGC TCT GTC CTC CTG CTG CAC CGA  2205
Leu Arg Pro Lys Ser Asp Glu Gly Ser Val Leo Leu Leu His Arg
            725                 730                 735

GCT TTG GGG GAT GAG GAC ACC AGC AGG GTG GAG AAG CTA GCT GCC  2250
Ala Leu Gly Asp Glu Asp Thr Ser Arg Val Glu Asn Leu Ala Ala
            740                 745                 750

AGT CTG CCA CTT CCG GAG TAC TGC GCC CTC CAT GGA AAA CTC AAC  2295
Ser Leu Pro Leu Pro Glu Tyr Cys Ala Leu His Gly Lys Leu Asn
            755                 760                 765

CTG GCT TCC TAC CTC CCA CCG GGC CTT GCC CTG CGT CCA CTG GAG  2340
Leu Ala Ser Tyr Leu Pro Pro Gly Leu Ala Leu Arg Pro Leu Glu
            770                 775                 780

CCC CAG CTC TGG GCA GCC TAT GGT GTG AGC CCG CAC CGG GGA CAC  2385
Pro Gln Leu Trp Ala Ala Tyr Gly Val Ser Pro His Arg Gly His
            785                 790                 795

CTG GGG ACC AAG AAC CTC TGT GTG GAG GTG GCC GAC CTG GTC AGC  2430
Leu Gly Thr Lys Asn Leu Cys Val Glu Val Ala Asp Leu Val Ser
            800                 805                 810

ATC CTG GTG CAT GCC GAC ACA CCA CTG CCT GCC TGG CAC CGG GCA  2475
Ile Leu Val His Ala Asp Thr Pro Leu Pro Ala Trp His Arg Ala
            815                 820                 825

CAG AAA GAC TTC CTT TCA GGC CTG GAC GGG GAG GGG CTC TGG TCT  2520
Gln Lys Asp Phe Leu Ser Gly Leu Asp Gly Glu Gly Leu Trp Ser
            830                 835                 840

CCG GGC AGC CAG GTC AGC ACT GTG TGG CAC GTG TTC CGG GCA CAG  2565
Pro Gly Ser Gln Val Ser Thr Val Trp His Val Phe Arg Ala Gln
            845                 850                 855

GAC GCC CAG CGC ATC CGC CGC TTT CTC CAG ATG GTG TGC CCG GCC  2610
```

TABLE I-continued

```
Asp Ala Gln Arg Ile Arg Arg Phe Leu Gln Met Val Cys Pro Ala
                860                 865                 870

GGG GCA GGC GCC CTG GAG CCT GGC GCC CCA GGC AGC TGC TAC CTG  2655
Gly Ala Gly Ala Leu Glu Pro Gly Ala Pro Gly Ser Cys Tyr Leu
                875                 880                 885

GAT GCA GGG CTG CGG CGG CGC CTG CGG GAG GAG TGG GGC GTG AGC  2700
Asp Ala Gly Leu Arg Arg Arg Leu Arg Glu Glu Trp Gly Val Ser
                890                 895                 900

TGC TGG ACC CTG CTC CAG GCC CCC GGA GAG GCC GTG CTG GTG CCT  2745
Cys Trp Thr Leu Leu Gln Ala Pro Gly Glu Ala Val Leu Val Pro
                905                 910                 915

GCA GGG GCT CCC CAC CAG GTG CAG GGC CTG GTG AGC ACA GTC AGC  2790
Ala Gly Ala Pro His Gln Val Gln Gly Leu Val Ser Thr Val Ser
                920                 925                 930

GTC ACT CAG CAC TTC CTC TCC CCT GAG ACC TCT GCC CTC TCT GCT  2335
Val Thr Gln His Phe Leu Ser Pro Glu Thr Ser Ala Leu Ser Ala
                935                 940                 945

CAG CTC TGC CAC CAG GGA CCC AGC CTT CCC CCT GAC TGC CAC CTG  2380
Gln Leu Cys His Gln Gly Pro Ser Leu Pro Pro Asp Cys His Leu
                950                 955                 960

CTT TAT GCC CAG ATG GAC TGG GCT GTG TTC CAA GCA GTG AAG GTG  2925
Leu Tyr Ala Gln Met Asp Trp Ala Val Phe Gln Ala Val Lys Val
                965                 970                 975

GCC GTG GGG ACA TTA CAG GAG GCC AAA TAG AGG GAT GCT AGG TGT  2970
Ala Val Gly Thr Leu Gln Glu Ala Lys
                980

CTG GGA TCG GGG TGG GGA CAG GTA GAC CAG GTG CTC AGC CCA GGC  3015

ACA ACT TCA GCA GGG GAT GGC GCT AGG GGA CTT GGG GAT TTC TGG  3060

TCA ACC CCA CAA GCA CCA CTC TGG GCA CAA GCA GGG CAC TCT GTT  3105

CCC CTC CCC CTT AAG CCA ACA ACC ACA GTG CCA CCA AGC TCA CAC  3150

CTG TCC TTC TCA GGC TGG CAT CTC CCC CAC CCT GTG CCC TTT TAT  3195

GTA CAG G                                                    3202
```

The hairless portion of the fusion protein used in the above transcription assays corresponds to rat hr positions 575–1215 (FIG. 1). Thus, from the conserved portions of amino acid sequence, a functionally equivalent fusion protein may be constructed with amino acid positions 575–1215 or 579–1215 of human Hr (FIG. 1). Given the sequence conservation between rat and mouse TRE elements, it is likely that human Hr and thyroid hormone receptor will bind to the rodent TRE elements and that a homologous Hr domain will be involved in binding to a nuclear hormone receptor (e.g., thyroid hormone receptor).

Also, the equivalent TRE element from the human genome will likely be similar to the rodent TRE element in the rodent hairless genes by sequence conservation. Thus, the human or rodent HR genes may be autoregulated by Hr protein or Hr-dependent.

Table II shows pairwise comparisons of the amino acid sequences for the human, rat, and mouse polypeptides. The first 26 amino acid residues of the rat polypeptide were not considered because it was longer than any other sequence. The numerator is the number of non-identical amino acids. The denominator is the total length of the polypeptide (i.e., 1189 amino acid residue) but it is only 984 amino acid residues in pairwise comparisons with SEQ ID NO:2 because of its shorter length. The predicted amino acid sequence of human Hr is about 98% identical to SEQ ID NO:3, but it is greater than 98% identical to SEQ ID NO:4.

The amino acid sequence of human Hr differs from the sequence of Ahmad et al. at 11 amino acid residues: 472 (Trp→Leu), 515 (Leu→Ala), 598 (Arg→Gly), 610 (Gly→Ser), 617 (Gly→Glu), 800 (Glu→Asp), 931 (Gly→Ala), 968 (Leu→Phe), 1047 (Asp→Arg), 1055 (Arg→Glu), and 1183 (Pro→Ala). But there are only differences between the amino acid sequence of human Hr and the sequence of Cichon et al. at three amino acid residues: 363 (Asp→Gly), 515 (Leu→Ala), and 617 (Gly→Glu).

These differences and the percent identity calculated for each pairwise comparison in Table II suggest that the human sequence published by Ahmad et al. contains one or more sequencing errors, or polymorphisms. Furthermore, Ahmad et al. report a missense mutation Thr1022Ala in all family members with congenital alopecia (a recessive disease), in the heterozygous state in obligate carriers, but absent in unaffected family members as well as 142 unrelated, unaffected individuals. The presence of the mutation identified by DNA sequencing was confirmed by heteroduplex analysis and restriction enzyme digestion. Ahmad et al. concluded that this adenine to guanine transition was not a normal polymorphic variant. In contrast, Cichon et al. find the mutation to be present in a heterozygous state at a frequency of 1.2% in a different control population (99% confidence level: 0.5% to 2.2%). If Thr1022Ala is a disease-causing recessive mutation, one would have expected the prevalence of congenital alopecia to be at least 1/40,000 (i.e., the expected frequency of homozygotes calculated from an allele frequency of 0.5%). Congenital alopecia, however, is a much rarer disease than 1/40,000. Therefore, Cichon et al. concluded that "Thr1022Ala is not, in and of itself, a deleterious change."

TABLE II

| | Rat | Mouse | Human | Ahmad et al. | Cichon et al. |
|---|---|---|---|---|---|
| SEQ ID NO:5 | 100% | | | | |
| SEQ ID NO:6 | 95.4% (1134/1189) | 100% | | | |
| SEQ ID NO:2 | 78.5% (772/984) | 80.1% (786/984) | 100% | | |
| SEQ ID NO:3 | 80.0 (951/1189) | 80.8% (961/1189) | 98.9% (11/984) | 100% | |
| SEQ ID NO:4 | 80.2% (953/1189) | 81.0% (963/1189) | 99.7% (3/984) | 99.1% (11/1189) | 100% |

Northern Blotting

A human multiple tissue Northern blot was purchased from Clontech and probed with a 3.5 Kb Eco RI-Xho I fragment from 37MC1. An approximately 5 Kb mRNA was clearly detected in brain and heart, and an approximately 1.4 Kb mRNA was detected in skeletal muscle. Other tissues (placenta, lung, liver, kidney, pancreas) do not show detectable HR mRNA Moreover, human brain multiple tissue Northern blots I and II were purchased from Clontech to determine the regions of the brain which expressed HR. An approximately 5 Kb mRNA was detected in amygdala, caudate nucleus, corpus callosum, hippocampus, hypothalamus, substantia nigra, subthalamic nucleus, thalamus, cerebral cortex, medulla, spinal cord, occipital pole, frontal lobe, temporal lobe, putamen, and cerebellum. An additional mRNA of approximately 5.5 Kb was detected only in cerebellum.

These results demonstrate that the invention may be used as a lineage marker using at least one of Hairless polynucleotide or polypeptide, or at least one specific binding molecule to the Hairless gene or its protein product (e.g., complementary polynucleotide, specific binder of Hr antigen). Specific cell lineages or developmental stages may be distinguished.

Southern Blotting

Genomic DNA was prepared from human blood, digested with appropriate restriction enzymes, separated on a 0.8% agarose gel, denatured in 0.5 M NaOH/1.5 M NaCl buffer, neutralized in 0.5 M TRIS (pH 7.4)/3 M NaCl buffer, and transferred to nitrocellulose membrane with 10×SSC buffer. A 3.0 Kb Kpn I fragment from 37MC12 was labeled by random priming, hybridized at 42° C. with the hybridization buffer used for library screening, washed at 65° C. with a wash buffer of 0.5×SSC/0.1% SDS, and then exposed with X-ray film for 20 hours in a −70° C. freezer. In separate, single restriction enzyme digestions, hybridizing fragments included four Bam HI fragments (about 9 Kb, 4 Kb, 2.1 Kb, 1.5 Kb); one Bgl II fragment (about 22 Kb); two Eco RI fragments (about 20 Kb, 7 Kb); one HindIII fragment (about 18 Kb); or one Xba I fragment (about 25 Kb). The foregoing and the chromosome localization results below are consistent with the human HR gene existing as a single copy gene in the haploid genome.

These results demonstrate that the invention may be used to distinguish between or among individuals in a human population by detection of at least one genetic polymorphism, to isolate and detect additional polymorphisms, to map other human genes with respect to the Hairless genetic locus, or to isolate and purify transcription regulatory regions which are genetically linked to the Hairless coding region. Specific hybridization and washing conditions are exemplified. A genomic clone containing the entire or partial coding sequence of the human Hairless gene may be selected from genomic DNA or a library thereof. Specific binding molecules to the human Hairless gene may also be derived.

Chromosome Localization

The plasmid containing the 3.5 Kb cDNA insert (clone 37MC1) of the human homolog of the mouse hairless gene was nick-translated with biotin-14 dATP (Gibco-BRL), with 20% incorporation as determined by tritium tracer incorporation. Slides with chromosome spreads were made from normal male lymphocytes cultured with BrdU (Bhatt et al., Nucleic Acids Res. 16, 3951–3961, 1988). Fluorescence in situ hybridization was performed as described (Lichter et al., Science 247, 64–69, 1990) with modifications. Probe mix (2×SSCP, 50% formamide, 10% dextran sulfate, 20 ng/$\mu$l biotinylated probe, and 200 $\mu$g/$\mu$l salmon sperm DNA) was denatured at 70° C. for 5 minutes, quickly chilled on ice, placed on slides and hybridized at 37° C. overnight. Slides were washed in 50% formamide/2×SSC at 37° C. for 20 minutes, and two changes of 2×SSC at 37° C. for 5 minutes each. Biotinylated probe was detected with FITC-avidin and amplified with biotinylated anti-avidin, using an in situ hybridization kit (Oncor) and manufacturer's instructions.

Analysis of 109 metaphase cells showed 20 cells (18%) had at least one pair of signals (involving both chromatids of a single chromosome). These 20 metaphases were photographed on color slide film (Kodak Ektachrome 400HC); 25 paired signals were seen. Of these, 22 (96%) were located on the p arm of a small C-group (chr. 8–12) chromosome and three were on other chromosomes (no other site had more than one signal). To determine the specific chromosome and band location of the signals, the hybridized slid was G-banded by FPG (fluorescence plus Giemsa), photographed and aligned with the color slides to determine subband location. Seventeen signals were analyzed after banding (an additional six signals were on a small C-group chromosome which was probably chromosome 8, but it could not be definitively identified, due to inadequate banding in those metaphases): 14 were on 8p12–21 and the remaining three signals were on different chromosomes (one each on 9p13, 14q12, 7q22).

These results demonstrate that the invention may be used as a marker for the chromosomal locus of the human Hairless gene. Other human genes may be mapped with respect to the locus; large-scale genetic alterations may be detected (e.g., amplification, duplication, deletion, inversion, translocation) and isolated by microdissection in the vicinity of the locus. This is another example of specific hybridization and washing conditions.

While the present invention has been described in connection with what is presently considered to be practical and preferred embodiments, it is understood that the present invention is not to be limited or restricted to the disclosed embodiments but, on the contrary, is intended to cover various modifications and equivalent arrangements included within the scope of the appended claims.

Thus, it is to be understood that variations in the described invention will be obvious to those skilled in the art without departing from the novel and non-obvious aspects of the present invention, and such variations are intended to come within the scope of the claims below.

I claim:

1. An isolated polypeptide having at least one biological activity of Hairless wherein, said activity is selected from the group consisting of transcriptional activity and the ability to bind thyroid hormone receptor, wherein said polypeptide is encoded by a polynucleotide containing at least one human nucleotide sequence of at least 250 contiguous nucleotides of SEQ ID NO:1 selected from the group consisting of:

(a) a nucleotide sequence which hybridizes to SEQ ID NO:1 under stringent hybridization conditions at 65° C. in a buffer of 500 mM $NaHPO_4$ pH 7.2, 7% SDS, 1% BSA, and 1 mM EDTA;

(b) a nucleotide sequence which has greater than 98% identity to SEQ ID NO:1, and, (c) a nucleotide sequence encoding at least 75 contiguous amino acids of SEQ ID NO:2.

2. The isolated polypeptide of claim 1, wherein said polypeptide has Hairless transcription factor activity.

3. The isolated polypeptide of claim 1, wherein the nucleotide sequence is at least 500 contiguous nucleotides of SEQ ID NO:1.

4. The isolated polypeptide of claim 1, wherein the nucleotide sequence is SEQ ID NO:1.

5. The isolated polypeptide of claim 1, comprising at least 100 contiguous amino acids of SEQ ID NO:2.

6. The isolated polypeptide of claim 5, comprising at least 250 contiguous amino acids of SEQ ID NO:2.

7. The isolated polypeptide of claim 1, wherein said polypeptide has the sequence of SEQ ID NO:2.

8. The polypeptide of claim 1 further comprising a heterologous polypeptide domain.

9. An isolated polypeptide having at least one biological activity of Hairless, wherein said activity is selected from the group consisting of transcriptional activity and the ability to bind thyroid hormone receptor, wherein said polypeptide is encoded by a polynucleotide containing at least one human nucleotide sequence selected from the group consisting of:

(a) a nucleotide sequence which is greater than 98% identical to SEQ ID NO:1, and (b) a nucleotide sequence encoding at least 75 contiguous amino acids of SEQ ID NO:2, wherein the nucleotide sequence is at least 50 nucleotides in length.

10. A method of screening in vitro for a chemical agent which modulates Hairless-mediated transcription comprising:

(a) incubating a candidate chemical agent, the polypeptide of claim 1 having transcriptional activity, and a reporter construct comprising a transcription regulatory region responsive to Hairless transcription factor operably linked to a reporter gene;

(b) measuring Hairless-dependent transcription of the reporter gene; and (c) identifying the chemical agent which modules Hairless-mediated transcription by a change in transcription of the reporter gene mediated by Hairless transcription factor activity.

11. The method of screening for a chemical agent of claim 10, wherein Hairless activity is increased by the identified chemical agent.

12. The method of screening for a chemical agent of claim 10, wherein Hairless activity is decreased by the identified chemical agent.

13. A method of screening in vitro for a chemical agent which modulates binding between Hairless and thyroid hormone receptor comprising:

(a) incubating a candidate chemical agent, the polypeptide of claim 1 having the ability to bind thyroid hormone receptor, and a polypeptide with thyroid hormone receptor activity;

(b) measuring binding of the polypeptide of claim 1 and the polypeptide with thyroid hormone receptor activity; and (c) identifying the chemical agent which modulates binding between Hairless and thyroid hormone receptor by detecting a change in binding between the polypeptide of claim 1 and the polypeptide with thyroid hormone receptor activity.

14. The method of screening for a chemical agent of claim 13, wherein the Hairless polypeptide is a fusion polypeptide immobilized on a solid support.

15. The method of screening for a chemical agent of claim 13, wherein the polypeptide with thyroid hormone receptor activity is a fusion polypeptide immobilized on a solid support.

16. The method of screening for a chemical agent of claim 13, wherein Hairless activity is increased by the identified chemical agent.

17. The method of screening for a chemical agent of claim 13, wherein Hairless activity is decreased by the identified chemical agent.

* * * * *

SEQUENCE LISTING

<160> NUMBER OF SEQ ID NOS: 10

<210> SEQ ID NO 1
<211> LENGTH: 3202
<212> TYPE: DNA
<213> ORGANISM: Homo sapiens

<400> SEQUENCE: 1
ttttactaca aggatccgag cattcccagg ttggcaaagg agcccttggc agctgcggaa 60
cctgggttgt ttggcttaaa ctctggtggg cacctgcaga gagccgggga ggccgaacgc 120
ccttcactgc accagaggga tggagagatg ggagctggcc ggcagcagaa tccttgcccg 180
ctcttcctgg ggcagccaga cactgtgccc tggacctcct ggcccgcttg tcccccaggc 240
cttgttcata ctcttggcaa cgtctgggct gggccaggcg atgggaacct tgggtaccag 300
ctggggccac cagcaacacc aaggtgcccc tctcctgagc cgcctgtcac ccagcggggc 360
tgctgttcat cctacccacc cactaaaggt ggggatcttg gcccttgtgg gaagtgccag 420
gagggcctgg agggggtgc cagtggagcc agcgaaccca gcgaggaagt gaacaaggcc 480
tctggcccca gggcctgtcc ccccagccac cacaccaagc tgaagaagac atggctcaca 540
cggcactcgg agcagtttga atgtccacgc ggctgccctg aggtcgagga gaggccggtt 600
gctcggctcc gggccctcaa aagggcaggc agcccccgagg tccagggagc aatgggcagt 660 ccagcccccca agcggccacc ggaccctttc ccaggcactg cagaacaggg ggctgggggt 720
tggcaggagg ttcgggacac atcgataggg aacaaggatg tggactcggg acagcatgat 780
gagcagaaag gaccccaaga tggccaggcc agtctccagg acccgggact tcaggacata 840
ccatgcctgc ttctccctgc aaaactggct caatgccaaa gttgtgccca ggcagctgga 900
gagggaggag ggcacgcctg ccactctcag caagtgcgga gatcgcctct gggaggggag 960
ctgcagcagg aggaagacac agccaccaac tccagctctg aggaaggccc agggtccggc 1020
cctgacagcc ggctcagcac aggcctcgcc aagcacctgc tcagtggttt gggggaccga 1080
ctgtgccgcc tgctgcggag ggagcgggag gccctggctt gggcccagcg ggaaggccaa 1140
gggccagccg tgacagggga cagcccaggc attccacgct gctgcagccg ttgccaccat 1200
ggactcttca acacccactg gcgatgtccc cgctgcagcc accggctgtg tgtggcctgt 1260
ggtcgtgtgg caggcactgg gcgggccagg gagaaagcag gctttcagga gcagtccgcg 1320
gaggagtgca cgcaggaggc cgggcacgct gcctgttccc tgatgctgac ccagtttgtc 1380
tccagccagg ctttggcaga gctgagcact gcaatgcacc aggtctgggt caagtttgat 1440
atccgggggc actgcccctg ccaagctgat gcccgggtat gggcccccgg ggatgcaggc 1500
cagcagaagg aatcaacaca gaaaacgccc ccaactccac aaccttcctg caatggcgac 1560
acccacagga ccaagagcat caaagaggag acccccgatt ccgctgagac cccagcagag 1620
gaccgtgctg gccgagggcc cctgccttgt ccttctctct gcgaactgct ggcttctacc 1680
gcggtcaaac tctgcttggg ccatgagcga atacacatgg ccttcgcccc cgtcactccg 1740
gccctgccca gtgatgaccg catcaccaac atcctggaca gcattatcgc acaggtggtg 1800
gaacggaaga tccaggagaa agccctgggg ccggggcttc gagctggccc gggtctgcgc 1860
aagggcctgg gcctgcccct ctctccagtg cggccccggc tgcctccccc aggggctttg 1920
ctgtggctgc aggagcccca gccttgccct cggcgtggct tccacctctt ccaggagcac 1980
tggaggcagg gccagcctgt gttggtgtca gggatccaaa ggacattgca gggcaacctg 2040

-continued

```
tgggggacag aagctcttgg ggcacttgga ggccaggtgc aggcgctgag ccccctcgga   2100

cctccccagc ccagcagcct gggcagcaca acattctggg agggcttctc ctggcctgag   2160

cttcgcccaa agtcagacga gggctctgtc ctcctgctgc accgagcttt gggggatgag   2220

gacaccagca gggtggagaa cctagctgcc agtctgccac ttccggagta ctgcgccctc   2280

catggaaaac tcaacctggc ttcctacctc ccaccgggcc ttgccctgcg tccactggag   2340

ccccagctct gggcagccta tggtgtgagc ccgcaccggg gacacctggg gaccaagaac   2400

ctctgtgtgg aggtggccga cctggtcagc atcctggtgc atgccgacac accactgcct   2460

gcctggcacc gggcacagaa agacttcctt tcaggcctgg acggggaggg gctctggtct   2520

ccgggcagcc aggtcagcac tgtgtggcac gtgttccggg cacaggacgc ccagcgcatc   2580

cgccgctttc tccagatggt gtgcccggcc ggggcaggcg ccctggagcc tggcgcccca   2640

ggcagctgct acctggatgc agggctgcgg cggcgcctgc gggaggagtg gggcgtgagc   2700

tgctggaccc tgctccaggc cccccggagag gccgtgctgg tgcctgcagg ggctccccac   2760

caggtgcagg gcctggtgag cacagtcagc gtcactcagc acttcctctc ccctgagacc   2820

tctgccctct ctgctcagct ctgccaccag ggacccagcc ttccccctga ctgccacctg   2880

ctttatgccc agatggactg ggctgtgttc caagcagtga aggtggccgt ggggacatta   2940

caggaggcca aatagaggga tgctaggtgt ctgggatcgg ggtggggaca ggtagaccag   3000

gtgctcagcc caggcacaac ttcagcaggg gatggcgcta ggggacttgg ggatttctgg   3060

tcaaccccac aagcaccact ctgggcacaa gcagggcact ctgttcccct ccccccttaag   3120

ccaacaacca cagtgccacc aagctcacac ctgtccttct caggctggca tctcccccac   3180

cctgtgccct tttatgtaca gg                                            3202


<210> SEQ ID NO 2
<211> LENGTH: 984
<212> TYPE: PRT
<213> ORGANISM: Homo sapiens

<400> SEQUENCE: 2

Phe Tyr Tyr Lys Asp Pro Ser Ile Pro Arg Leu Ala Lys Glu Pro Leu
1               5                   10                  15

Ala Ala Ala Glu Pro Gly Leu Phe Gly Leu Asn Ser Gly Gly His Leu
            20                  25                  30

Gln Arg Ala Gly Glu Ala Glu Arg Pro Ser Leu His Gln Arg Asp Gly
        35                  40                  45

Glu Met Gly Ala Gly Arg Gln Gln Asn Pro Cys Pro Leu Phe Leu Gly
    50                  55                  60

Gln Pro Asp Thr Val Pro Trp Thr Ser Trp Pro Ala Cys Pro Pro Gly
65                  70                  75                  80

Leu Val His Thr Leu Gly Asn Val Trp Ala Gly Pro Gly Asp Gly Asn
                85                  90                  95

Leu Gly Tyr Gln Leu Gly Pro Pro Ala Thr Pro Arg Cys Pro Ser Pro
            100                 105                 110

Glu Pro Pro Val Thr Gln Arg Gly Cys Cys Ser Ser Tyr Pro Pro Thr
        115                 120                 125

Lys Gly Gly Asp Leu Gly Pro Cys Gly Lys Cys Gln Glu Gly Leu Glu
    130                 135                 140

Gly Gly Ala Ser Gly Ala Ser Glu Pro Ser Glu Glu Val Asn Lys Ala
145                 150                 155                 160
```

-continued

```
Ser Gly Pro Arg Ala Cys Pro Pro Ser His His Thr Lys Leu Lys Lys
                165                 170                 175

Thr Trp Leu Thr Arg His Ser Glu Gln Phe Glu Cys Pro Arg Gly Cys
            180                 185                 190

Pro Glu Val Glu Glu Arg Pro Val Ala Arg Leu Arg Ala Leu Lys Arg
        195                 200                 205

Ala Gly Ser Pro Glu Val Gln Gly Ala Met Gly Ser Pro Ala Pro Lys
    210                 215                 220

Arg Pro Pro Asp Pro Phe Pro Gly Thr Ala Glu Gln Gly Ala Gly Gly
225                 230                 235                 240

Trp Gln Glu Val Arg Asp Thr Ser Ile Gly Asn Lys Asp Val Asp Ser
                245                 250                 255

Gly Gln His Asp Glu Gln Lys Gly Pro Gln Asp Gly Gln Ala Ser Leu
            260                 265                 270

Gln Asp Pro Gly Leu Gln Asp Ile Pro Cys Leu Ala Leu Pro Ala Lys
        275                 280                 285

Leu Ala Gln Cys Gln Ser Cys Ala Gln Ala Ala Gly Glu Gly Gly Gly
    290                 295                 300

His Ala Cys His Ser Gln Gln Val Arg Arg Ser Pro Leu Gly Gly Glu
305                 310                 315                 320

Leu Gln Gln Glu Glu Asp Thr Ala Thr Asn Ser Ser Ser Glu Glu Gly
                325                 330                 335

Pro Gly Ser Gly Pro Asp Ser Arg Leu Ser Thr Gly Leu Ala Lys His
            340                 345                 350

Leu Leu Ser Gly Leu Gly Asp Arg Leu Cys Arg Leu Leu Arg Arg Glu
        355                 360                 365

Arg Glu Ala Leu Ala Trp Ala Gln Arg Glu Gly Gln Gly Pro Ala Val
    370                 375                 380

Thr Gly Asp Ser Pro Gly Ile Pro Arg Cys Cys Ser Arg Cys His His
385                 390                 395                 400

Gly Leu Phe Asn Thr His Trp Arg Cys Pro Arg Cys Ser His Arg Leu
                405                 410                 415

Cys Val Ala Cys Gly Arg Val Ala Gly Thr Gly Arg Ala Arg Glu Lys
            420                 425                 430

Ala Gly Phe Gln Glu Gln Ser Ala Glu Glu Cys Thr Gln Glu Ala Gly
        435                 440                 445

His Ala Ala Cys Ser Leu Met Leu Thr Gln Phe Val Ser Ser Gln Ala
    450                 455                 460

Leu Ala Glu Leu Ser Thr Ala Met His Gln Val Trp Val Lys Phe Asp
465                 470                 475                 480

Ile Arg Gly His Cys Pro Cys Gln Ala Asp Ala Arg Val Trp Ala Pro
                485                 490                 495

Gly Asp Ala Gly Gln Gln Lys Glu Ser Thr Gln Lys Thr Pro Pro Thr
            500                 505                 510

Pro Gln Pro Ser Cys Asn Gly Asp Thr His Arg Thr Lys Ser Ile Lys
        515                 520                 525

Glu Glu Thr Pro Asp Ser Ala Glu Thr Pro Ala Glu Asp Arg Ala Gly
    530                 535                 540

Arg Gly Pro Leu Pro Cys Pro Ser Leu Cys Glu Leu Leu Ala Ser Thr
545                 550                 555                 560

Ala Val Lys Leu Cys Leu Gly His Glu Arg Ile His Met Ala Phe Ala
                565                 570                 575

Pro Val Thr Pro Ala Leu Pro Ser Asp Asp Arg Ile Thr Asn Ile Leu
```

-continued

```
            580                 585                 590

Asp Ser Ile Ile Ala Gln Val Val Glu Arg Lys Ile Gln Glu Lys Ala
        595                 600                 605

Leu Gly Pro Gly Leu Arg Ala Gly Pro Gly Leu Arg Lys Gly Leu Gly
    610                 615                 620

Leu Pro Leu Ser Pro Val Arg Pro Arg Leu Pro Pro Pro Gly Ala Leu
625                 630                 635                 640

Leu Trp Leu Gln Glu Pro Gln Pro Cys Pro Arg Arg Gly Phe His Leu
                645                 650                 655

Phe Gln Glu His Trp Arg Gln Gly Gln Pro Val Leu Val Ser Gly Ile
            660                 665                 670

Gln Arg Thr Leu Gln Gly Asn Leu Trp Gly Thr Glu Ala Leu Gly Ala
        675                 680                 685

Leu Gly Gly Gln Val Gln Ala Leu Ser Pro Leu Gly Pro Pro Gln Pro
    690                 695                 700

Ser Ser Leu Gly Ser Thr Thr Phe Trp Glu Gly Phe Ser Trp Pro Glu
705                 710                 715                 720

Leu Arg Pro Lys Ser Asp Glu Gly Ser Val Leu Leu Leu His Arg Ala
                725                 730                 735

Leu Gly Asp Glu Asp Thr Ser Arg Val Glu Asn Leu Ala Ala Ser Leu
            740                 745                 750

Pro Leu Pro Glu Tyr Cys Ala Leu His Gly Lys Leu Asn Leu Ala Ser
        755                 760                 765

Tyr Leu Pro Pro Gly Leu Ala Leu Arg Pro Leu Glu Pro Gln Leu Trp
    770                 775                 780

Ala Ala Tyr Gly Val Ser Pro His Arg Gly His Leu Gly Thr Lys Asn
785                 790                 795                 800

Leu Cys Val Glu Val Ala Asp Leu Val Ser Ile Leu Val His Ala Asp
                805                 810                 815

Thr Pro Leu Pro Ala Trp His Arg Ala Gln Lys Asp Phe Leu Ser Gly
            820                 825                 830

Leu Asp Gly Glu Gly Leu Trp Ser Pro Gly Ser Gln Val Ser Thr Val
        835                 840                 845

Trp His Val Phe Arg Ala Gln Asp Ala Gln Arg Ile Arg Arg Phe Leu
    850                 855                 860

Gln Met Val Cys Pro Ala Gly Ala Gly Ala Leu Glu Pro Gly Ala Pro
865                 870                 875                 880

Gly Ser Cys Tyr Leu Asp Ala Gly Leu Arg Arg Arg Leu Arg Glu Glu
                885                 890                 895

Trp Gly Val Ser Cys Trp Thr Leu Leu Gln Ala Pro Gly Glu Ala Val
            900                 905                 910

Leu Val Pro Ala Gly Ala Pro His Gln Val Gln Gly Leu Val Ser Thr
        915                 920                 925

Val Ser Val Thr Gln His Phe Leu Ser Pro Glu Thr Ser Ala Leu Ser
    930                 935                 940

Ala Gln Leu Cys His Gln Gly Pro Ser Leu Pro Pro Asp Cys His Leu
945                 950                 955                 960

Leu Tyr Ala Gln Met Asp Trp Ala Val Phe Gln Ala Val Lys Val Ala
                965                 970                 975

Val Gly Thr Leu Gln Glu Ala Lys
            980

<210> SEQ ID NO 3
```

-continued

<211> LENGTH: 1189
<212> TYPE: PRT
<213> ORGANISM: Homo sapiens

<400> SEQUENCE: 3

Met Glu Ser Thr Pro Ser Phe Leu Lys Gly Thr Pro Thr Trp Glu Lys
1 5 10 15

Thr Ala Pro Glu Asn Gly Ile Val Arg Gln Glu Pro Gly Ser Pro Pro
20 25 30

Arg Asp Gly Leu His His Gly Pro Leu Cys Leu Gly Glu Pro Ala Pro
35 40 45

Phe Trp Arg Gly Val Leu Ser Thr Pro Asp Ser Trp Leu Pro Pro Gly
50 55 60

Phe Pro Gln Gly Pro Lys Asp Met Leu Pro Leu Val Glu Gly Glu Gly
65 70 75 80

Pro Gln Asn Gly Glu Arg Lys Val Asn Trp Leu Gly Ser Lys Glu Gly
85 90 95

Leu Arg Trp Lys Glu Ala Met Leu Thr His Pro Leu Ala Phe Cys Gly
100 105 110

Pro Ala Cys Pro Pro Arg Cys Gly Pro Leu Met Pro Glu His Ser Gly
115 120 125

Gly His Leu Lys Ser Asp Pro Val Ala Phe Arg Pro Trp His Cys Pro
130 135 140

Phe Leu Leu Glu Thr Lys Ile Leu Glu Arg Ala Pro Phe Trp Val Pro
145 150 155 160

Thr Cys Leu Pro Pro Tyr Leu Val Ser Gly Leu Pro Pro Glu His Pro
165 170 175

Cys Asp Trp Pro Leu Thr Pro His Pro Trp Val Tyr Ser Gly Gly Gln
180 185 190

Pro Lys Val Pro Ser Ala Phe Ser Leu Gly Ser Lys Gly Phe Tyr Tyr
195 200 205

Lys Asp Pro Ser Ile Pro Arg Leu Ala Lys Glu Pro Leu Ala Ala Ala
210 215 220

Glu Pro Gly Leu Phe Gly Leu Asn Ser Gly Gly His Leu Gln Arg Ala
225 230 235 240

Gly Glu Ala Glu Arg Pro Ser Leu His Gln Arg Asp Gly Glu Met Gly
245 250 255

Ala Gly Arg Gln Gln Asn Pro Cys Pro Leu Phe Leu Gly Gln Pro Asp
260 265 270

Thr Val Pro Trp Thr Ser Trp Pro Ala Cys Pro Pro Gly Leu Val His
275 280 285

Thr Leu Gly Asn Val Trp Ala Gly Pro Gly Asp Gly Asn Leu Gly Tyr
290 295 300

Gln Leu Gly Pro Pro Ala Thr Pro Arg Cys Pro Ser Pro Glu Pro Pro
305 310 315 320

Val Thr Gln Arg Gly Cys Cys Ser Ser Tyr Pro Pro Thr Lys Gly Gly
325 330 335

Asp Leu Gly Pro Cys Gly Lys Cys Gln Glu Gly Leu Glu Gly Gly Ala
340 345 350

Ser Gly Ala Ser Glu Pro Ser Glu Glu Val Asn Lys Ala Ser Gly Pro
355 360 365

Arg Ala Cys Pro Pro Ser His His Thr Lys Leu Lys Lys Thr Trp Leu
370 375 380

Thr Arg His Ser Glu Gln Phe Glu Cys Pro Arg Gly Cys Pro Glu Val

-continued

```
385                 390                 395                 400

Glu Glu Arg Pro Val Ala Arg Leu Arg Ala Leu Lys Arg Ala Gly Ser
                405                 410                 415

Pro Glu Val Gln Gly Ala Met Gly Ser Pro Ala Pro Lys Arg Pro Pro
            420                 425                 430

Asp Pro Phe Pro Gly Thr Ala Glu Gln Gly Ala Gly Gly Leu Gln Glu
        435                 440                 445

Val Arg Asp Thr Ser Ile Gly Asn Lys Asp Val Asp Ser Gly Gln His
    450                 455                 460

Asp Glu Gln Lys Gly Pro Gln Asp Gly Gln Ala Ser Leu Gln Asp Pro
465                 470                 475                 480

Gly Leu Gln Asp Ile Pro Cys Leu Ala Leu Pro Ala Lys Leu Ala Gln
                485                 490                 495

Cys Gln Ser Cys Ala Gln Ala Ala Gly Glu Gly Gly Gly His Ala Cys
            500                 505                 510

His Ser Gln Gln Val Arg Arg Ser Pro Leu Gly Gly Glu Leu Gln Gln
        515                 520                 525

Glu Glu Asp Thr Ala Thr Asn Ser Ser Ser Glu Glu Gly Pro Gly Ser
    530                 535                 540

Gly Pro Asp Ser Arg Leu Ser Thr Gly Leu Ala Lys His Leu Leu Ser
545                 550                 555                 560

Gly Leu Gly Asp Arg Leu Cys Arg Leu Leu Arg Gly Glu Arg Glu Ala
                565                 570                 575

Leu Ala Trp Ala Gln Arg Glu Ser Gln Gly Pro Ala Val Thr Glu Asp
            580                 585                 590

Ser Pro Gly Ile Pro Arg Cys Cys Ser Arg Cys His His Gly Leu Phe
        595                 600                 605

Asn Thr His Trp Arg Cys Pro Arg Cys Ser His Arg Leu Cys Val Ala
    610                 615                 620

Cys Gly Arg Val Ala Gly Thr Gly Arg Ala Arg Glu Lys Ala Gly Phe
625                 630                 635                 640

Gln Glu Gln Ser Ala Glu Glu Cys Thr Gln Glu Ala Gly His Ala Ala
                645                 650                 655

Cys Ser Leu Met Leu Thr Gln Phe Val Ser Ser Gln Ala Leu Ala Glu
            660                 665                 670

Leu Ser Thr Ala Met His Gln Val Trp Val Lys Phe Asp Ile Arg Gly
        675                 680                 685

His Cys Pro Cys Gln Ala Asp Ala Arg Val Trp Ala Pro Gly Asp Ala
    690                 695                 700

Gly Gln Gln Lys Glu Ser Thr Gln Lys Thr Pro Pro Thr Pro Gln Pro
705                 710                 715                 720

Ser Cys Asn Gly Asp Thr His Arg Thr Lys Ser Ile Lys Glu Glu Thr
                725                 730                 735

Pro Asp Ser Ala Glu Thr Pro Ala Glu Asp Arg Ala Gly Arg Gly Pro
            740                 745                 750

Leu Pro Cys Pro Ser Leu Cys Glu Leu Leu Ala Ser Thr Ala Val Lys
        755                 760                 765

Leu Cys Leu Gly His Asp Arg Ile His Met Ala Phe Ala Pro Val Thr
    770                 775                 780

Pro Ala Leu Pro Ser Asp Asp Arg Ile Thr Asn Ile Leu Asp Ser Ile
785                 790                 795                 800

Ile Ala Gln Val Val Glu Arg Lys Ile Gln Glu Lys Ala Leu Gly Pro
                805                 810                 815
```

-continued

```
Gly Leu Arg Ala Gly Pro Gly Leu Arg Lys Gly Leu Gly Leu Pro Leu
            820                 825                 830

Ser Pro Val Arg Pro Arg Leu Pro Pro Pro Gly Ala Leu Leu Trp Leu
        835                 840                 845

Gln Glu Pro Gln Pro Cys Pro Arg Arg Gly Phe His Leu Phe Gln Glu
    850                 855                 860

His Trp Arg Gln Gly Gln Pro Val Leu Val Ser Gly Ile Gln Arg Thr
865                 870                 875                 880

Leu Gln Gly Asn Leu Trp Gly Thr Glu Ala Leu Gly Ala Leu Gly Gly
                885                 890                 895

Gln Val Gln Ala Leu Ser Pro Leu Ala Pro Pro Gln Pro Ser Ser Leu
            900                 905                 910

Gly Ser Thr Thr Phe Trp Glu Gly Phe Ser Trp Pro Glu Leu Arg Pro
        915                 920                 925

Lys Ser Asp Glu Gly Ser Val Leu Leu Leu His Arg Ala Phe Gly Asp
    930                 935                 940

Glu Asp Thr Ser Arg Val Glu Asn Leu Ala Ala Ser Leu Pro Leu Pro
945                 950                 955                 960

Glu Tyr Cys Ala Leu His Gly Lys Leu Asn Leu Ala Ser Tyr Leu Pro
                965                 970                 975

Pro Gly Leu Ala Leu Arg Pro Leu Glu Pro Gln Leu Trp Ala Ala Tyr
            980                 985                 990

Gly Val Ser Pro His Arg Gly His Leu Gly Thr Lys Asn Leu Cys Val
        995                 1000                1005

Glu Val Ala Asp Leu Val Ser Ile Leu Val His Ala Arg Thr Pro Leu
   1010                1015                1020

Pro Ala Trp His Glu Ala Gln Lys Asp Phe Leu Ser Gly Leu Asp Gly
1025                1030                1035                1040

Glu Gly Leu Trp Ser Pro Gly Ser Gln Val Ser Thr Val Trp His Val
               1045                1050                1055

Phe Arg Ala Gln Asp Ala Gln Arg Ile Arg Arg Phe Leu Gln Met Val
           1060                1065                1070

Cys Pro Ala Gly Ala Gly Ala Leu Glu Pro Gly Ala Pro Gly Ser Cys
       1075                1080                1085

Tyr Leu Asp Ala Gly Leu Arg Arg Arg Leu Arg Glu Glu Trp Gly Val
   1090                1095                1100

Ser Cys Trp Thr Leu Leu Gln Ala Pro Gly Glu Ala Val Leu Val Pro
1105                1110                1115                1120

Ala Gly Ala Pro His Gln Val Gln Gly Leu Val Ser Thr Val Ser Val
               1125                1130                1135

Thr Gln His Phe Leu Ser Pro Glu Thr Ser Ala Leu Ser Ala Gln Leu
           1140                1145                1150

Cys His Gln Gly Ala Ser Leu Pro Pro Asp Cys His Leu Leu Tyr Ala
       1155                1160                1165

Gln Met Asp Trp Ala Val Phe Gln Ala Val Lys Val Ala Val Gly Thr
   1170                1175                1180

Leu Gln Glu Ala Lys
1185
```

<210> SEQ ID NO 4
<211> LENGTH: 1189
<212> TYPE: PRT
<213> ORGANISM: Homo sapiens -continued

<400> SEQUENCE: 4

```
Met Glu Ser Thr Pro Ser Phe Leu Lys Gly Thr Pro Thr Trp Glu Lys
  1               5                  10                  15

Thr Ala Pro Glu Asn Gly Ile Val Arg Gln Glu Pro Gly Ser Pro Pro
             20                  25                  30

Arg Asp Gly Leu His His Gly Pro Leu Cys Leu Gly Glu Pro Ala Pro
         35                  40                  45

Phe Trp Arg Gly Val Leu Ser Thr Pro Asp Ser Trp Leu Pro Pro Gly
     50                  55                  60

Phe Pro Gln Gly Pro Lys Asp Met Leu Pro Leu Val Glu Gly Glu Gly
 65                  70                  75                  80

Pro Gln Asn Gly Glu Arg Lys Val Asn Trp Leu Gly Ser Lys Glu Gly
                 85                  90                  95

Leu Arg Trp Lys Glu Ala Met Leu Thr His Pro Leu Ala Phe Cys Gly
            100                 105                 110

Pro Ala Cys Pro Pro Arg Cys Gly Pro Leu Met Pro Glu His Ser Gly
        115                 120                 125

Gly His Leu Lys Ser Asp Pro Val Ala Phe Arg Pro Trp His Cys Pro
    130                 135                 140

Phe Leu Leu Glu Thr Lys Ile Leu Glu Arg Ala Pro Phe Trp Val Pro
145                 150                 155                 160

Thr Cys Leu Pro Pro Tyr Leu Val Ser Gly Leu Pro Pro Glu His Pro
                165                 170                 175

Cys Asp Trp Pro Leu Thr Pro His Pro Trp Val Tyr Ser Gly Gly Gln
            180                 185                 190

Pro Lys Val Pro Ser Ala Phe Ser Leu Gly Ser Lys Gly Phe Tyr Tyr
        195                 200                 205

Lys Asp Pro Ser Ile Pro Arg Leu Ala Lys Glu Pro Leu Ala Ala Ala
    210                 215                 220

Glu Pro Gly Leu Phe Gly Leu Asn Ser Gly Gly His Leu Gln Arg Ala
225                 230                 235                 240

Gly Glu Ala Glu Arg Pro Ser Leu His Gln Arg Asp Gly Glu Met Gly
                245                 250                 255

Ala Gly Arg Gln Gln Asn Pro Cys Pro Leu Phe Leu Gly Gln Pro Asp
            260                 265                 270

Thr Val Pro Trp Thr Ser Trp Pro Ala Cys Pro Pro Gly Leu Val His
        275                 280                 285

Thr Leu Gly Asn Val Trp Ala Gly Pro Gly Asp Gly Asn Leu Gly Tyr
    290                 295                 300

Gln Leu Gly Pro Pro Ala Thr Pro Arg Cys Pro Ser Pro Glu Pro Pro
305                 310                 315                 320

Val Thr Gln Arg Gly Cys Cys Ser Ser Tyr Pro Pro Thr Lys Gly Gly
                325                 330                 335

Gly Leu Gly Pro Cys Gly Lys Cys Gln Glu Gly Leu Glu Gly Gly Ala
            340                 345                 350

Ser Gly Ala Ser Glu Pro Ser Glu Glu Val Asn Lys Ala Ser Gly Pro
        355                 360                 365

Arg Ala Cys Pro Pro Ser His His Thr Lys Leu Lys Lys Thr Trp Leu
    370                 375                 380

Thr Arg His Ser Glu Gln Phe Glu Cys Pro Arg Gly Cys Pro Glu Val
385                 390                 395                 400

Glu Glu Arg Pro Val Ala Arg Leu Arg Ala Leu Lys Arg Ala Gly Ser
                405                 410                 415
```

-continued

```
Pro Glu Val Gln Gly Ala Met Gly Ser Pro Ala Pro Lys Arg Pro Pro
            420                 425                 430

Asp Pro Phe Pro Gly Thr Ala Glu Gln Gly Ala Gly Gly Trp Gln Glu
        435                 440                 445

Val Arg Asp Thr Ser Ile Gly Asn Lys Asp Val Asp Ser Gly Gln His
    450                 455                 460

Asp Glu Gln Lys Gly Pro Gln Asp Gly Gln Ala Ser Leu Gln Asp Pro
465                 470                 475                 480

Gly Leu Gln Asp Ile Pro Cys Leu Ala Leu Pro Ala Lys Leu Ala Gln
                485                 490                 495

Cys Gln Ser Cys Ala Gln Ala Ala Gly Glu Gly Gly Gly His Ala Cys
            500                 505                 510

His Ser Gln Gln Val Arg Arg Ser Pro Leu Gly Gly Glu Leu Gln Gln
        515                 520                 525

Glu Glu Asp Thr Ala Thr Asn Ser Ser Ser Glu Glu Gly Pro Gly Ser
    530                 535                 540

Gly Pro Asp Ser Arg Leu Ser Thr Gly Leu Ala Lys His Leu Leu Ser
545                 550                 555                 560

Gly Leu Gly Asp Arg Leu Cys Arg Leu Leu Arg Arg Glu Arg Glu Ala
                565                 570                 575

Leu Ala Trp Ala Gln Arg Glu Gly Gln Gly Pro Ala Val Thr Glu Asp
            580                 585                 590

Ser Pro Gly Ile Pro Arg Cys Cys Ser Arg Cys His His Gly Leu Phe
        595                 600                 605

Asn Thr His Trp Arg Cys Pro Arg Cys Ser His Arg Leu Cys Val Ala
    610                 615                 620

Cys Gly Arg Val Ala Gly Thr Gly Arg Ala Arg Glu Lys Ala Gly Phe
625                 630                 635                 640

Gln Glu Gln Ser Ala Glu Glu Cys Thr Gln Glu Ala Gly His Ala Ala
                645                 650                 655

Cys Ser Leu Met Leu Thr Gln Phe Val Ser Ser Gln Ala Leu Ala Glu
            660                 665                 670

Leu Ser Thr Ala Met His Gln Val Trp Val Lys Phe Asp Ile Arg Gly
        675                 680                 685

His Cys Pro Cys Gln Ala Asp Ala Arg Val Trp Ala Pro Gly Asp Ala
    690                 695                 700

Gly Gln Gln Lys Glu Ser Thr Gln Lys Thr Pro Pro Thr Pro Gln Pro
705                 710                 715                 720

Ser Cys Asn Gly Asp Thr His Arg Thr Lys Ser Ile Lys Glu Glu Thr
                725                 730                 735

Pro Asp Ser Ala Glu Thr Pro Ala Glu Asp Arg Ala Gly Arg Gly Pro
            740                 745                 750

Leu Pro Cys Pro Ser Leu Cys Glu Leu Leu Ala Ser Thr Ala Val Lys
        755                 760                 765

Leu Cys Leu Gly His Glu Arg Ile His Met Ala Phe Ala Pro Val Thr
    770                 775                 780

Pro Ala Leu Pro Ser Asp Asp Arg Ile Thr Asn Ile Leu Asp Ser Ile
785                 790                 795                 800

Ile Ala Gln Val Val Glu Arg Lys Ile Gln Glu Lys Ala Leu Gly Pro
                805                 810                 815

Gly Leu Arg Ala Gly Pro Gly Leu Arg Lys Gly Leu Gly Leu Pro Leu
            820                 825                 830
```

-continued

```
Ser Pro Val Arg Pro Arg Leu Pro Pro Pro Gly Ala Leu Leu Trp Leu
        835                 840                 845

Gln Glu Pro Gln Pro Cys Pro Arg Arg Gly Phe His Leu Phe Gln Glu
    850                 855                 860

His Trp Arg Gln Gly Gln Pro Val Leu Val Ser Gly Ile Gln Arg Thr
865                 870                 875                 880

Leu Gln Gly Asn Leu Trp Gly Thr Glu Ala Leu Gly Ala Leu Gly Gly
                885                 890                 895

Gln Val Gln Ala Leu Ser Pro Leu Gly Pro Pro Gln Pro Ser Ser Leu
            900                 905                 910

Gly Ser Thr Thr Phe Trp Glu Gly Phe Ser Trp Pro Glu Leu Arg Pro
        915                 920                 925

Lys Ser Asp Glu Gly Ser Val Leu Leu Leu His Arg Ala Leu Gly Asp
    930                 935                 940

Glu Asp Thr Ser Arg Val Glu Asn Leu Ala Ala Ser Leu Pro Leu Pro
945                 950                 955                 960

Glu Tyr Cys Ala Leu His Gly Lys Leu Asn Leu Ala Ser Tyr Leu Pro
                965                 970                 975

Pro Gly Leu Ala Leu Arg Pro Leu Glu Pro Gln Leu Trp Ala Ala Tyr
            980                 985                 990

Gly Val Ser Pro His Arg Gly His Leu Gly Thr Lys Asn Leu Cys Val
        995                 1000                1005

Glu Val Ala Asp Leu Val Ser Ile Leu Val His Ala Asp Thr Pro Leu
   1010                 1015                1020

Pro Ala Trp His Arg Ala Gln Lys Asp Phe Leu Ser Gly Leu Asp Gly
1025                1030                1035                1040

Glu Gly Leu Trp Ser Pro Gly Ser Gln Val Ser Thr Val Trp His Val
               1045                1050                1055

Phe Arg Ala Gln Asp Ala Gln Arg Ile Arg Arg Phe Leu Gln Met Val
           1060                1065                1070

Cys Pro Ala Gly Ala Gly Ala Leu Glu Pro Gly Ala Pro Gly Ser Cys
       1075                1080                1085

Tyr Leu Asp Ala Gly Leu Arg Arg Arg Leu Arg Glu Glu Trp Gly Val
   1090                1095                1100

Ser Cys Trp Thr Leu Leu Gln Ala Pro Gly Glu Ala Val Leu Val Pro
1105                1110                1115                1120

Ala Gly Ala Pro His Gln Val Gln Gly Leu Val Ser Thr Val Ser Val
               1125                1130                1135

Thr Gln His Phe Leu Ser Pro Glu Thr Ser Ala Leu Ser Ala Gln Leu
           1140                1145                1150

Cys His Gln Gly Pro Ser Leu Pro Pro Asp Cys His Leu Leu Tyr Ala
       1155                1160                1165

Gln Met Asp Trp Ala Val Phe Gln Ala Val Lys Val Ala Val Gly Thr
   1170                1175                1180

Leu Gln Glu Ala Lys
1185


<210> SEQ ID NO 5
<211> LENGTH: 1207
<212> TYPE: PRT
<213> ORGANISM: Rat

<400> SEQUENCE: 5

Met Gly Leu Arg Ser Ser Cys Phe Val Leu Thr Leu Gln Asp Pro Pro
  1               5                  10                  15
```

-continued

```
Leu Gly Glu Pro His Glu Gly Arg Arg Val Met Glu Ser Met Pro Ser
                20                  25                  30

Phe Leu Lys Asp Thr Pro Ala Trp Glu Lys Thr Ala Pro Val Asn Gly
        35                  40                  45

Ile Val Gly Gln Glu Pro Gly Thr Ser Pro Gln Asp Gly Leu His His
    50                  55                  60

Gly Ala Leu Cys Leu Gly Glu Pro Val Pro Phe Trp Arg Gly Val Leu
65                  70                  75                  80

Ser Ala Pro Asp Ser Trp Leu Pro Pro Gly Phe Leu Gln Gly Pro Lys
                85                  90                  95

Asp Thr Leu Ser Val Val Glu Gly Glu Gly Ser Arg Asn Gly Glu Arg
            100                 105                 110

Lys Ala Asn Trp Leu Gly Ser Lys Glu Gly Leu Arg Trp Lys Glu Ala
        115                 120                 125

Met Leu Ala His Pro Leu Ala Phe Cys Gly Pro Ala Cys Pro Pro Arg
    130                 135                 140

Tyr Gly Pro Leu Ile Pro Glu His Ser Ser Gly His Pro Lys Ser Asp
145                 150                 155                 160

Pro Val Ala Phe Arg Pro Leu His Cys Pro Phe Leu Leu Glu Thr Lys
                165                 170                 175

Ile Leu Glu Arg Ala Pro Phe Trp Val Pro Thr Cys Leu Pro Pro Tyr
            180                 185                 190

Leu Met Ser Ser Leu Pro Pro Glu Arg Ser Tyr Asp Trp Pro Leu Ala
        195                 200                 205

Pro Ser Pro Trp Val Tyr Ser Gly Ser Gln Pro Lys Val Pro Ser Ala
    210                 215                 220

Phe Ser Leu Gly Ser Lys Gly Phe Tyr His Lys Asp Pro Asn Ile Leu
225                 230                 235                 240

Arg Pro Ala Lys Glu Pro Leu Ala Ala Ser Glu Ser Gly Met Leu Gly
                245                 250                 255

Leu Ala Pro Gly Gly His Leu Gln Gln Ala Cys Asp Ala Glu Gly Pro
            260                 265                 270

Ser Leu His Gln Arg Asp Gly Glu Thr Gly Ala Gly Arg Gln Gln Asn
        275                 280                 285

Leu Cys Pro Val Phe Leu Gly Tyr Pro Asp Thr Val Pro Arg Thr Pro
    290                 295                 300

Trp Pro Ser Cys Pro Pro Gly Leu Val His Thr Leu Gly Asn Val Trp
305                 310                 315                 320

Ala Gly Pro Gly Ser Asn Ser Phe Gly Tyr Gln Leu Gly Pro Pro Val
                325                 330                 335

Thr Pro Arg Cys Pro Ser Pro Gly Pro Pro Thr Pro Pro Gly Gly Cys
            340                 345                 350

Cys Ser Ser His Leu Pro Ala Arg Glu Gly Asp Pro Gly Pro Cys Arg
        355                 360                 365

Lys Cys Gln Asp Ser Pro Glu Gly Ser Ser Ser Gly Pro Gly Glu Ser
    370                 375                 380

Ser Glu Glu Arg Asn Lys Ala Gly Ser Arg Ala Ser Pro Pro Ser His
385                 390                 395                 400

His Thr Lys Leu Lys Lys Thr Trp Leu Thr Arg His Ser Glu Gln Phe
                405                 410                 415

Glu Cys Pro Gly Gly Cys Pro Gly Lys Gly Glu Ser Pro Ala Thr Gly
            420                 425                 430
```

-continued

```
Leu Arg Ala Leu Lys Arg Ala Gly Ser Pro Glu Val Gln Gly Ala Arg
        435                 440                 445

Gly Pro Ala Pro Lys Arg Pro Ser His Thr Phe Pro Gly Thr Gly Arg
    450                 455                 460

Gln Gly Ala Arg Ala Trp Gln Glu Thr Pro Glu Thr Ser Thr Gly Ser
465                 470                 475                 480

Lys Ala Glu Ala Gln Gln Gln Glu Glu Gln Arg Gly Pro Arg Asp Gly
                485                 490                 495

Arg Ile Arg Leu Arg Glu Ser Arg Leu Glu Asp Thr Ser Cys Gln His
            500                 505                 510

His Leu Ala Gly Val Thr Gln Cys Pro Ser Cys Val Gln Ala Ala Gly
        515                 520                 525

Glu Val Glu Ile Leu Thr Ser His Ser Gln Lys Ser His Lys Leu Pro
    530                 535                 540

Leu Glu Glu Lys Pro Leu Glu Glu Asp Ser Cys Ala Thr Ser Glu Glu
545                 550                 555                 560

Gly Gly Gly Ser Ser Pro Glu Ala Ser Ile Asn Lys Gly Leu Ala Lys
                565                 570                 575

His Leu Leu Ser Gly Leu Gly Asp Arg Leu Cys Arg Leu Leu Arg Lys
            580                 585                 590

Glu Arg Glu Ala Leu Ala Trp Ala Gln Arg Glu Gly Gln Gly Pro Ala
        595                 600                 605

Met Thr Glu Asp Ser Pro Gly Ile Pro His Cys Cys Ser Arg Cys His
    610                 615                 620

His Gly Leu Phe Asn Thr His Trp Arg Cys Ser His Cys Ser His Arg
625                 630                 635                 640

Leu Cys Val Ala Cys Gly Arg Ile Ala Gly Ala Gly Lys Asn Arg Glu
                645                 650                 655

Lys Thr Gly Ser Arg Glu Gln Arg Thr Asp Asp Cys Ala Gln Glu Ala
            660                 665                 670

Gly His Ala Ala Cys Ser Leu Ile Leu Thr Gln Phe Val Ser Ser Gln
        675                 680                 685

Ala Leu Ala Glu Leu Ser Thr Val Met His Gln Val Trp Ala Lys Phe
    690                 695                 700

Asp Ile Arg Gly His Cys Phe Cys Gln Val Asp Ala Arg Val Trp Ala
705                 710                 715                 720

Pro Gly Asp Gly Gly Gln Gln Lys Glu Pro Thr Glu Lys Thr Pro Pro
                725                 730                 735

Ala Pro Gln Leu Ser Cys Asn Gly Asp Ser Asn Arg Thr Lys Asp Ile
            740                 745                 750

Lys Glu Glu Thr Pro Asp Ser Thr Glu Ser Pro Ala Glu Asp Arg Ala
        755                 760                 765

Gly Arg Ser Pro Leu Pro Cys Pro Ser Leu Cys Glu Leu Leu Ala Ser
    770                 775                 780

Thr Ala Val Lys Leu Cys Leu Gly His Glu Arg Ile His Met Ala Phe
785                 790                 795                 800

Ala Pro Val Thr Pro Ala Leu Pro Ser Asp Asp Arg Ile Thr Asn Ile
                805                 810                 815

Leu Asp Ser Ile Ile Ala Gln Val Val Glu Arg Lys Ile Gln Glu Lys
            820                 825                 830

Ala Leu Gly Pro Gly Leu Arg Ala Gly Ser Gly Leu Arg Lys Gly Leu
        835                 840                 845

Ser Leu Pro Leu Ser Pro Val Arg Thr Gln Leu Ser Pro Pro Gly Ala
```

-continued

```
    850                 855                 860

Leu Leu Trp Leu Gln Glu Pro Arg Pro Lys His Gly Phe Arg Leu Phe
865                 870                 875                 880

Gln Glu His Trp Arg Gln Gly Gln Pro Val Leu Val Ser Gly Ile Gln
                885                 890                 895

Lys Thr Leu Arg Leu Ser Leu Trp Gly Met Glu Ala Leu Gly Thr Leu
            900                 905                 910

Gly Gly Gln Val Gln Thr Leu Thr Ala Leu Gly Pro Pro Gln Pro Thr
        915                 920                 925

Ser Leu Asp Ser Thr Ala Phe Trp Lys Gly Phe Ser His Pro Glu Ala
    930                 935                 940

Arg Pro Lys Leu Asp Glu Gly Ser Val Leu Leu Leu His Arg Pro Leu
945                 950                 955                 960

Gly Asp Lys Asp Glu Ser Arg Val Glu Asn Leu Ala Ser Ser Leu Pro
                965                 970                 975

Leu Pro Glu Tyr Cys Ala His Gln Gly Lys Leu Asn Leu Ala Ser Tyr
            980                 985                 990

Leu Pro Leu Gly Leu Thr Leu His Pro Leu Glu Pro Gln Leu Trp Ala
        995                 1000                1005

Ala Tyr Gly Val Asn Ser His Arg Gly His Leu Gly Thr Lys Asn Leu
   1010                1015                1020

Cys Val Glu Val Ser Asp Leu Ile Ser Ile Leu Val His Ala Glu Ala
1025                1030                1035                1040

Gln Leu Pro Pro Trp Tyr Arg Ala Gln Lys Asp Phe Leu Ser Gly Leu
               1045                1050                1055

Asp Gly Glu Gly Leu Trp Ser Pro Gly Ser Gln Thr Ser Thr Val Trp
           1060                1065                1070

His Val Phe Arg Ala Gln Asp Ala Gln Arg Ile Arg Arg Phe Leu Gln
       1075                1080                1085

Met Val Cys Pro Ala Gly Ala Gly Thr Leu Glu Pro Gly Ala Pro Gly
   1090                1095                1100

Ser Cys Tyr Leu Asp Ser Gly Leu Arg Arg Arg Leu Arg Glu Glu Trp
1105                1110                1115                1120

Gly Val Ser Cys Trp Thr Leu Leu Gln Ala Pro Gly Glu Ala Val Leu
               1125                1130                1135

Val Pro Ala Gly Ala Pro His Gln Val Gln Gly Leu Val Ser Thr Ile
           1140                1145                1150

Ser Val Thr Gln His Phe Leu Ser Pro Glu Thr Ser Ala Leu Ser Ala
       1155                1160                1165

Gln Leu Cys His Gln Gly Ala Ser Leu Pro Pro Asp His Arg Met Leu
   1170                1175                1180

Tyr Ala Gln Met Asp Arg Ala Val Phe Gln Ala Val Lys Val Ala Val
1185                1190                1195                1200

Gly Thr Leu Gln Glu Ala Lys
               1205


<210> SEQ ID NO 6
<211> LENGTH: 1182
<212> TYPE: PRT
<213> ORGANISM: Mouse

<400> SEQUENCE: 6

Met Glu Ser Met Pro Ser Phe Leu Lys Asp Thr Pro Ala Trp Glu Lys
  1               5                  10                  15
```

-continued

```
Thr Ala Pro Val Asn Gly Ile Val Gly Gln Glu Pro Gly Thr Ser Pro
            20                  25                  30

Gln Asp Gly Leu Arg His Gly Ala Leu Cys Leu Gly Glu Pro Ala Pro
        35                  40                  45

Phe Trp Arg Gly Val Leu Ser Thr Pro Asp Ser Trp Leu Pro Pro Gly
    50                  55                  60

Phe Leu Gln Gly Pro Lys Asp Thr Leu Ser Leu Val Glu Gly Glu Gly
 65                  70                  75                  80

Pro Arg Asn Gly Glu Arg Lys Gly Ser Trp Leu Gly Gly Lys Glu Gly
                85                  90                  95

Leu Arg Trp Lys Glu Ala Met Leu Ala His Pro Leu Ala Phe Cys Gly
            100                 105                 110

Pro Ala Cys Pro Pro Arg Tyr Gly Pro Leu Ile Pro Glu His Ser Gly
        115                 120                 125

Gly His Pro Lys Ser Asp Pro Val Ala Phe Arg Pro Leu His Cys Pro
    130                 135                 140

Phe Leu Leu Glu Thr Lys Ile Leu Glu Arg Ala Pro Phe Trp Val Pro
145                 150                 155                 160

Thr Cys Leu Pro Pro Tyr Leu Met Ser Ser Leu Pro Pro Glu Arg Pro
                165                 170                 175

Tyr Asp Trp Pro Leu Ala Pro Asn Pro Trp Val Tyr Ser Gly Ser Gln
            180                 185                 190

Pro Lys Val Pro Ser Ala Phe Gly Leu Gly Ser Lys Gly Phe Tyr His
        195                 200                 205

Lys Asp Pro Asn Ile Leu Arg Pro Ala Lys Glu Pro Leu Ala Glu Ser
    210                 215                 220

Gly Met Leu Gly Leu Ala Pro Gly Gly His Leu Gln Gln Ala Cys Glu
225                 230                 235                 240

Ser Glu Gly Pro Ser Leu His Gln Arg Asp Gly Glu Thr Gly Ala Gly
                245                 250                 255

Arg Gln Gln Asn Leu Cys Pro Val Phe Leu Gly Tyr Pro Asp Thr Val
            260                 265                 270

Pro Arg Ala Pro Trp Pro Ser Cys Pro Pro Gly Leu Val His Ser Leu
        275                 280                 285

Gly Asn Ile Trp Ala Gly Pro Gly Ser Asn Ser Leu Gly Tyr Gln Leu
    290                 295                 300

Gly Pro Pro Ala Thr Pro Arg Cys Pro Ser Pro Gly Pro Pro Thr Pro
305                 310                 315                 320

Pro Gly Gly Cys Cys Ser Ser His Leu Pro Ala Arg Glu Gly Asp Leu
                325                 330                 335

Gly Pro Cys Arg Lys Cys Gln Asp Ser Pro Glu Gly Gly Ser Ser Gly
            340                 345                 350

Pro Gly Glu Ser Ser Glu Glu Arg Asn Lys Ala Asp Ser Arg Ala Cys
        355                 360                 365

Pro Pro Ser His His Thr Lys Leu Lys Lys Thr Trp Leu Thr Arg His
    370                 375                 380

Ser Glu Gln Phe Glu Cys Pro Gly Gly Cys Ser Gly Lys Glu Glu Ser
385                 390                 395                 400

Ser Ala Thr Gly Leu Arg Ala Leu Lys Arg Ala Gly Ser Pro Glu Val
                405                 410                 415

Gln Gly Ala Ser Arg Gly Pro Ala Pro Lys Arg Pro Ser His Pro Phe
            420                 425                 430

Pro Gly Thr Gly Arg Gln Gly Ala Arg Ala Trp Gln Glu Thr Pro Glu
```

-continued

```
        435                 440                 445

Thr Ile Ile Gly Ser Lys Ala Glu Ala Glu Gln Gln Glu Glu Gln Arg
    450                 455                 460

Gly Pro Arg Asp Gly Arg Ile Arg Leu Gln Glu Ser Arg Leu Val Asp
465                 470                 475                 480

Thr Ser Cys Gln His His Leu Ala Gly Val Thr Gln Cys Gln Ser Cys
                485                 490                 495

Val Gln Ala Ala Gly Glu Val Gly Val Leu Thr Gly His Ser Gln Lys
            500                 505                 510

Ser Arg Arg Ser Pro Leu Glu Glu Lys Gln Leu Glu Glu Glu Asp Ser
        515                 520                 525

Ser Ala Thr Ser Glu Glu Gly Gly Gly Gly Pro Gly Pro Glu Ala Ser
    530                 535                 540

Leu Asn Lys Gly Leu Ala Lys His Leu Leu Ser Gly Leu Gly Asp Arg
545                 550                 555                 560

Leu Cys Arg Leu Leu Arg Lys Glu Arg Glu Ala Leu Ala Trp Ala Gln
                565                 570                 575

Arg Glu Gly Gln Gly Pro Ala Met Thr Glu Asp Ser Pro Gly Ile Pro
            580                 585                 590

His Cys Cys Ser Arg Cys His His Gly Leu Phe Asn Thr His Trp Arg
        595                 600                 605

Cys Ser His Cys Ser His Arg Leu Cys Val Ala Cys Gly Arg Ile Ala
    610                 615                 620

Gly Ala Gly Lys Asn Arg Glu Lys Thr Gly Ser Gln Glu Gln His Thr
625                 630                 635                 640

Asp Asp Cys Ala Gln Glu Ala Gly His Ala Ala Cys Ser Leu Ile Leu
                645                 650                 655

Thr Gln Phe Val Ser Ser Gln Ala Leu Ala Glu Leu Ser Thr Val Met
            660                 665                 670

His Gln Val Trp Ala Lys Phe Asp Ile Arg Gly His Cys Phe Cys Gln
        675                 680                 685

Val Asp Ala Arg Val Trp Ala Pro Gly Asp Gly Gly Gln Gln Lys Glu
    690                 695                 700

Pro Thr Glu Lys Thr Pro Pro Thr Pro Gln Pro Ser Cys Asn Gly Asp
705                 710                 715                 720

Ser Asn Arg Thr Lys Asp Ile Lys Glu Glu Thr Pro Asp Ser Thr Glu
                725                 730                 735

Ser Pro Ala Glu Asp Gly Ala Gly Arg Ser Pro Leu Pro Cys Pro Ser
            740                 745                 750

Leu Cys Glu Leu Leu Ala Ser Thr Ala Val Lys Leu Cys Leu Gly His
        755                 760                 765

Asp Arg Ile His Met Ala Phe Ala Pro Val Thr Pro Ala Leu Pro Ser
    770                 775                 780

Asp Asp Arg Ile Thr Asn Ile Leu Asp Ser Ile Ile Ala Gln Val Val
785                 790                 795                 800

Glu Arg Lys Ile Gln Glu Lys Ala Leu Gly Pro Gly Leu Arg Ala Gly
                805                 810                 815

Ser Gly Leu Arg Lys Gly Leu Ser Leu Pro Leu Ser Pro Val Arg Thr
            820                 825                 830

Arg Leu Ser Pro Pro Gly Ala Leu Leu Trp Leu Gln Glu Pro Arg Pro
        835                 840                 845

Lys His Gly Phe His Leu Phe Gln Glu His Trp Arg Gln Gly Gln Pro
    850                 855                 860
```

-continued

```
Val Leu Val Ser Gly Ile Gln Lys Thr Leu Arg Leu Ser Leu Trp Gly
865                 870                 875                 880

Met Glu Ala Leu Gly Thr Leu Gly Gly Gln Val Gln Thr Leu Thr Ala
                885                 890                 895

Leu Gly Pro Pro Gln Pro Thr Asn Leu Asp Ser Thr Ala Phe Trp Glu
            900                 905                 910

Gly Phe Ser His Pro Glu Thr Arg Pro Lys Leu Asp Glu Gly Ser Val
        915                 920                 925

Leu Leu Leu His Arg Thr Leu Gly Asp Lys Asp Ala Ser Arg Val Gln
    930                 935                 940

Asn Leu Ala Ser Ser Leu Pro Leu Pro Glu Tyr Cys Ala His Gln Gly
945                 950                 955                 960

Lys Leu Asn Leu Ala Ser Tyr Leu Pro Leu Gly Leu Thr Leu His Pro
                965                 970                 975

Leu Glu Pro Gln Leu Trp Ala Ala Tyr Gly Val Asn Ser His Arg Gly
            980                 985                 990

His Leu Gly Thr Lys Asn Leu Cys Val Glu Val Ser Asp Leu Ile Ser
        995                 1000                1005

Ile Leu Val His Ala Glu Ala Gln Leu Pro Pro Trp Tyr Arg Ala Gln
   1010                1015                1020

Lys Asp Phe Leu Ser Gly Leu Asp Gly Glu Gly Leu Trp Ser Pro Gly
1025               1030                1035                1040

Ser Gln Thr Ser Thr Val Trp His Val Phe Arg Ala Gln Asp Ala Gln
               1045                1050                1055

Arg Ile Arg Arg Phe Leu Gln Met Val Cys Pro Ala Gly Ala Gly Thr
           1060                1065                1070

Leu Glu Pro Gly Ala Pro Gly Ser Cys Tyr Leu Asp Ala Gly Leu Arg
       1075                1080                1085

Arg Arg Leu Arg Glu Glu Trp Gly Val Ser Cys Trp Thr Leu Leu Gln
   1090                1095                1100

Ala Pro Gly Glu Ala Val Leu Val Pro Ala Gly Ala Pro His Gln Val
1105               1110                1115                1120

Gln Gly Leu Val Ser Thr Ile Ser Val Thr Gln His Phe Leu Ser Pro
               1125                1130                1135

Glu Thr Ser Ala Leu Ser Ala Gln Leu Tyr His Gln Gly Ala Ser Leu
           1140                1145                1150

Pro Pro Asp His Arg Met Leu Tyr Ala Gln Met Asp Arg Ala Val Phe
       1155                1160                1165

Gln Ala Val Lys Ala Ala Val Gly Ala Leu Gln Glu Ala Lys
   1170                1175                1180


<210> SEQ ID NO 7
<211> LENGTH: 111
<212> TYPE: DNA
<213> ORGANISM: Rat

<400> SEQUENCE: 7

agtcaggcca agctgccact aatccgggcg gggagagggg gggcacccac gtcagagcgg     60

ggactgccgg gtggagggca tctgaggaca tcccctccca ctcacgcggc c            111


<210> SEQ ID NO 8
<211> LENGTH: 111
<212> TYPE: DNA
<213> ORGANISM: Mouse
```

-continued

```
<400> SEQUENCE: 8

agtcaggcca atctgccact aatccgggcg gggagagggg gggcacccac ctcagagcgg     60

ggactgccgg gtggagggca tctgaggaca tcccctccca ctcacgcagc c             111


<210> SEQ ID NO 9
<211> LENGTH: 23
<212> TYPE: DNA
<213> ORGANISM: Rat

<400> SEQUENCE: 9

ggtggagggc atctgaggac atc                                              23


<210> SEQ ID NO 10
<211> LENGTH: 21
<212> TYPE: DNA
<213> ORGANISM: Rat

<400> SEQUENCE: 10

tggagggcat ctgaggacat c                                                21
```